United States Patent
Wexler et al.

(10) Patent No.: US 9,542,613 B2
(45) Date of Patent: Jan. 10, 2017

(54) SYSTEMS AND METHODS FOR PROCESSING IMAGES

(71) Applicants: Yonatan Wexler, Jerusalem (IL); Amnon Shashua, Mevaseret Zion (IL)

(72) Inventors: Yonatan Wexler, Jerusalem (IL); Amnon Shashua, Mevaseret Zion (IL)

(73) Assignee: OrCam Technologies Ltd., Jerusalem (IL)

( * ) Notice: Subject to any disclaimer, the term of this patent is extended or adjusted under 35 U.S.C. 154(b) by 0 days.

(21) Appl. No.: 14/135,928

(22) Filed: Dec. 20, 2013

(65) Prior Publication Data

US 2014/0267652 A1 Sep. 18, 2014

Related U.S. Application Data

(60) Provisional application No. 61/799,649, filed on Mar. 15, 2013, provisional application No. 61/830,122, filed on Jun. 2, 2013.

(51) Int. Cl.
*H04N 5/232* (2006.01)
*G06K 9/32* (2006.01)
(Continued)

(52) U.S. Cl.
CPC .............. *G06K 9/3275* (2013.01); *A61F 9/08* (2013.01); *G06F 3/011* (2013.01); *G06F 3/16* (2013.01);
(Continued)

(58) Field of Classification Search
None
See application file for complete search history.

(56) References Cited

U.S. PATENT DOCUMENTS

| 6,115,482 A | 9/2000 | Sears et al. |
| 7,929,016 B2 * | 4/2011 | Yoshida et al. ............... 348/159 |

(Continued)

FOREIGN PATENT DOCUMENTS

| EP | 2065871 | 6/2009 |
| EP | 2490155 A1 | 8/2012 |

(Continued)

OTHER PUBLICATIONS

U.S. Appl. No. 14/136,438, filed Dec. 20, 2013, entitled "Apparatus, Method, and Computer Readable Medium for Expedited Text Reading Using Staged OCR Technique,".

(Continued)

*Primary Examiner* — Frederick Bailey
(74) *Attorney, Agent, or Firm* — Finnegan, Henderson, Farabow, Garrett & Dunner, LLP

(57) ABSTRACT

A apparatus and method are provided for processing images. In one embodiment, the apparatus includes an image sensor configured to capture real time images from an environment of a user. The apparatus also includes a mobile power source, and at least one processor device configured to process, at an initial resolution, images to determine existence of a trigger, and access rules associating image context with image capture resolution to enable images of a first context to be processed at a lower capture resolution than images of a second context. The processor device analyzes at least one first image, selects a first image capture resolution rule, and applies the first image capture resolution rule to a subsequent captured image. The processor device analyzes at least one second image, selects a second image capture resolution rule, and applies the second image capture resolution rule to a second subsequent captured image.

24 Claims, 21 Drawing Sheets

(51) Int. Cl.

| | | |
|---|---|---|
| G09B 21/00 | (2006.01) | |
| G06K 9/00 | (2006.01) | |
| G06K 9/22 | (2006.01) | |
| A61F 9/08 | (2006.01) | |
| G08B 3/10 | (2006.01) | |
| G08B 6/00 | (2006.01) | |
| G06F 17/27 | (2006.01) | |
| G06K 9/74 | (2006.01) | |
| G10L 13/04 | (2013.01) | |
| G06F 3/16 | (2006.01) | |
| G06F 3/01 | (2006.01) | |
| H04N 5/225 | (2006.01) | |
| G06K 9/20 | (2006.01) | |
| G01B 11/24 | (2006.01) | |
| G06T 7/00 | (2006.01) | |
| G06K 9/30 | (2006.01) | |
| G02C 11/00 | (2006.01) | |

(52) U.S. Cl.
CPC ....... *G06F 17/2765* (2013.01); *G06K 9/00221* (2013.01); *G06K 9/00288* (2013.01); *G06K 9/00442* (2013.01); *G06K 9/00463* (2013.01); *G06K 9/00469* (2013.01); *G06K 9/00483* (2013.01); *G06K 9/00671* (2013.01); *G06K 9/2081* (2013.01); *G06K 9/22* (2013.01); *G06K 9/325* (2013.01); *G06K 9/3233* (2013.01); *G06K 9/3241* (2013.01); *G06K 9/3283* (2013.01); *G06K 9/74* (2013.01); *G08B 3/10* (2013.01); *G08B 6/00* (2013.01); *G09B 21/00* (2013.01); *G09B 21/001* (2013.01); *G09B 21/003* (2013.01); *G09B 21/006* (2013.01); *G10L 13/043* (2013.01); *H04N 5/2251* (2013.01); *H04N 5/2252* (2013.01); *H04N 5/23229* (2013.01); *H04N 5/23232* (2013.01); *G01B 11/24* (2013.01); *G02C 11/10* (2013.01); *G06K 9/00852* (2013.01); *G06K 9/30* (2013.01); *G06K 2009/00489* (2013.01); *G06K 2009/2045* (2013.01); *G06T 7/0051* (2013.01)

(56) References Cited

U.S. PATENT DOCUMENTS

| | | |
|---|---|---|
| 2005/0208457 A1 | 9/2005 | Fink et al. |
| 2006/0013483 A1 | 1/2006 | Kurzweil et al. |
| 2006/0017810 A1 | 1/2006 | Kurzweil et al. |
| 2006/0044398 A1* | 3/2006 | Foong et al. ............ 348/207.99 |
| 2008/0297586 A1* | 12/2008 | Kurtz et al. ............ 348/14.08 |
| 2009/0110386 A1 | 4/2009 | Kamada et al. |
| 2009/0219387 A1* | 9/2009 | Marman et al. ............ 348/143 |
| 2010/0150449 A1* | 6/2010 | Laksono ........................ 382/190 |
| 2011/0102588 A1* | 5/2011 | Trundle et al. ............ 348/143 |
| 2012/0212593 A1 | 8/2012 | Na'aman et al. |
| 2013/0169536 A1 | 7/2013 | Wexler et al. |
| 2013/0271584 A1 | 10/2013 | Wexler et al. |

FOREIGN PATENT DOCUMENTS

| | | |
|---|---|---|
| GB | 2452124 A | 2/2009 |
| GB | 2490785 A | 11/2012 |

OTHER PUBLICATIONS

U.S. Appl. No. 14/135,727, filed Dec. 20, 2013, entitled "Systems and Method for Audible Facial Recognition,".
U.S. Appl. No. 14/137,033, filed Dec. 20, 2013, entitled "Apparatus and Method for Providing Failed-Attempt Feedback Using a Camera on Glasses,".
U.S. Appl. No. 14/137,263, filed Dec. 20, 2013, entitled "Apparatus and Method for Executing System Commands Based on Captured Image Data,".
U.S. Appl. No. 14/135,757, filed Dec. 20, 2013, entitled "Systems and Methods for Automatic Control of a Continuous Action,".
U.S. Appl. No. 14/137,373, filed Dec. 20, 2013, entitled "Apparatus and Method for Automatic Action Selection Based on Image Context,".
U.S. Appl. No. 14/135,762, filed Dec. 20, 2013, entitled "Systems and Methods for Performing a Triggered Action,".
U.S. Appl. No. 14/137,328, filed Dec. 20, 2013, entitled "Apparatus and Method for Performing Actions Based on Captured Image Data,".
U.S. Appl. No. 14/135,859, filed Dec. 20, 2013, entitled "Apparatus Connectable to Glasses,".
U.S. Appl. No. 14/137,446, filed Dec. 20, 2013, entitled "Apparatus and Method for Hierarchical Object Identification Using a Camera on Glasses,".
U.S. Appl. No. 14/135,775, filed Dec. 20, 2013, entitled "Systems and Methods for Providing Feedback Based on the State of an Object,".
U.S. Appl. No. 14/137,522, filed Dec. 20, 2013, entitled "Apparatus and Method for Using Background Change to Determine Context,".
U.S. Appl. No. 14/136,545, filed Dec. 20, 2013, entitled "Apparatus, Method, and Computer Readable Medium for Recognizing Text on a Curved Surface,".
U.S. Appl. No. 14/137,384, filed Dec. 20, 2013, entitled "Systems and Methods for Audibly Presenting Textual Information Included in Image Data,".
U.S. Appl. No. 14/136,876, filed Dec. 20, 2013, entitled "Apparatus and Method for Analyzing Images,".
Karacs, Kristof et al., "Bionic Eyeglass: An Audio Guide for Visually Impaired," Biomedical Circuits and Systems Conference, 2006, BIOCAS 2006, IEEE, Piscataway, NJ, Nov. 39, 2006, p. 190-193.
Lai, Chin-Lun et al., "An Integrated Portable Vision Assistant Agency for the Visual Impaired People," 2009 IEEE International Conference on Control and Automation, Christchurch, New Zealand, Dec. 9-11, 2009 (6 pages).
De Jager et al., A low-power, distributed, pervasive healthcare system for supporting memory, Proceedings of the International Symposium on Mobile Ad Hoc Networking and Computing; Jan. 1, 2011, 8 pages.
International Search Report and Written Opinion in PCT/IB2014/000969, mailed Aug. 6, 2014, 11 pages.

* cited by examiner

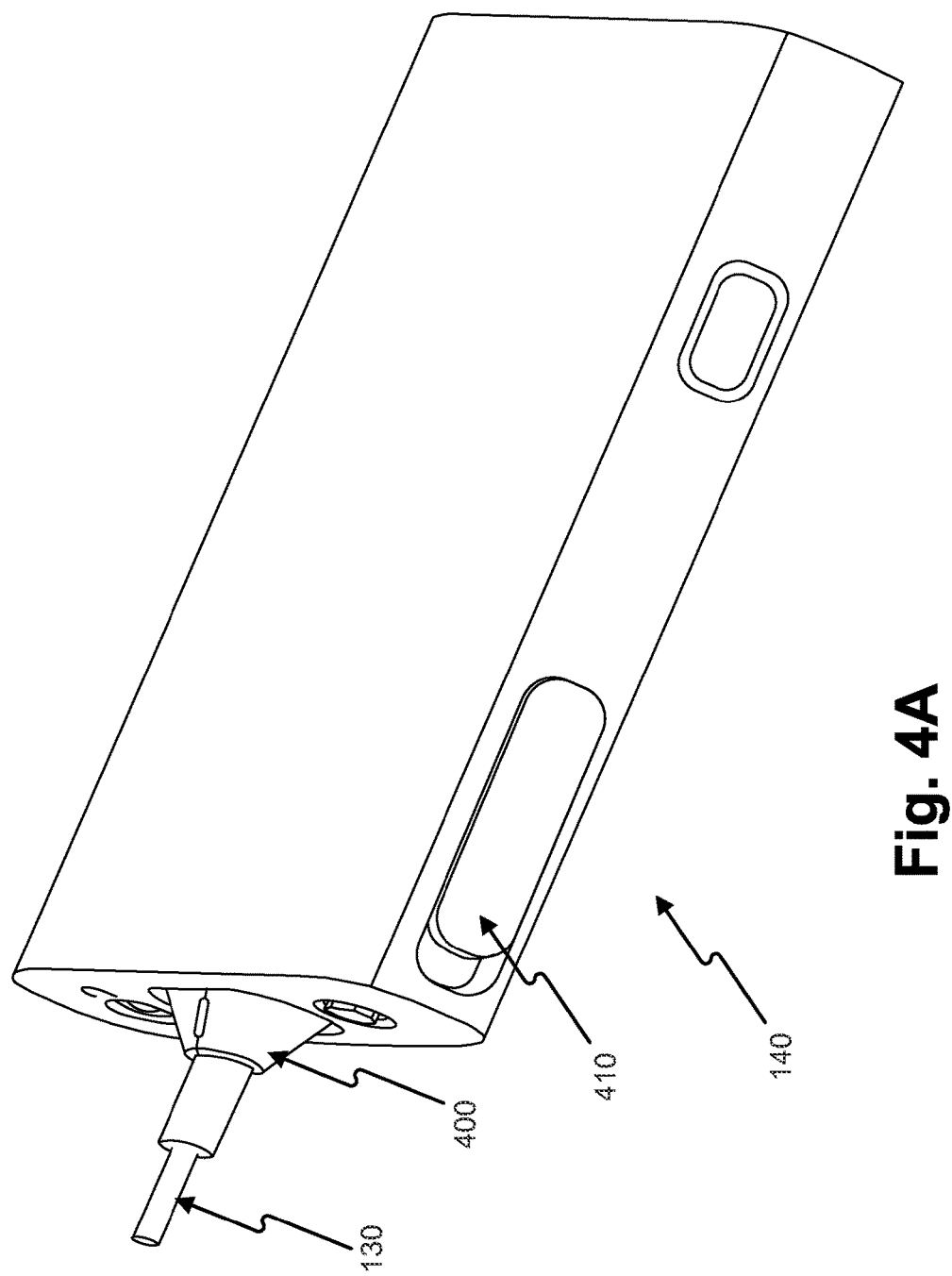

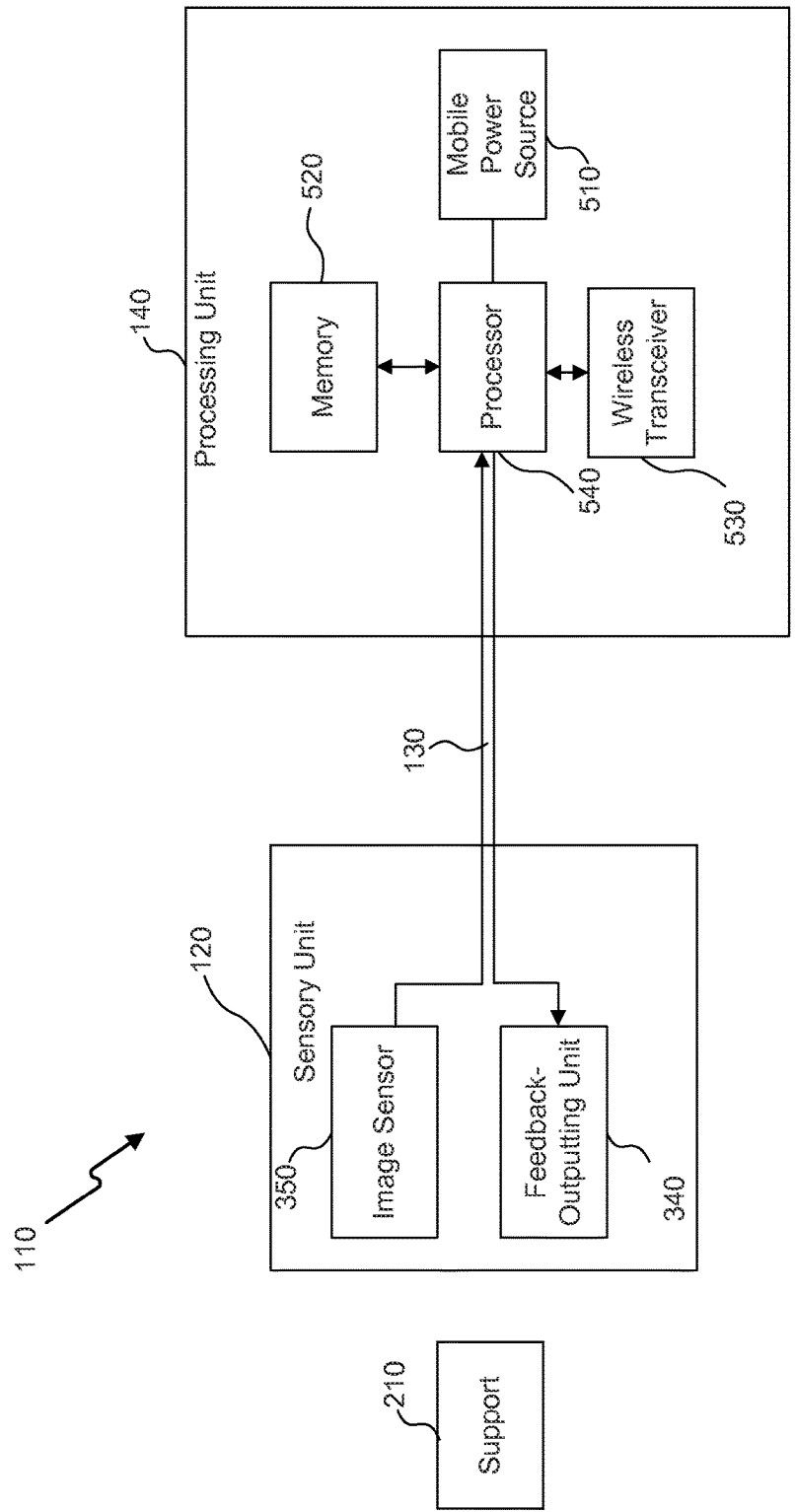

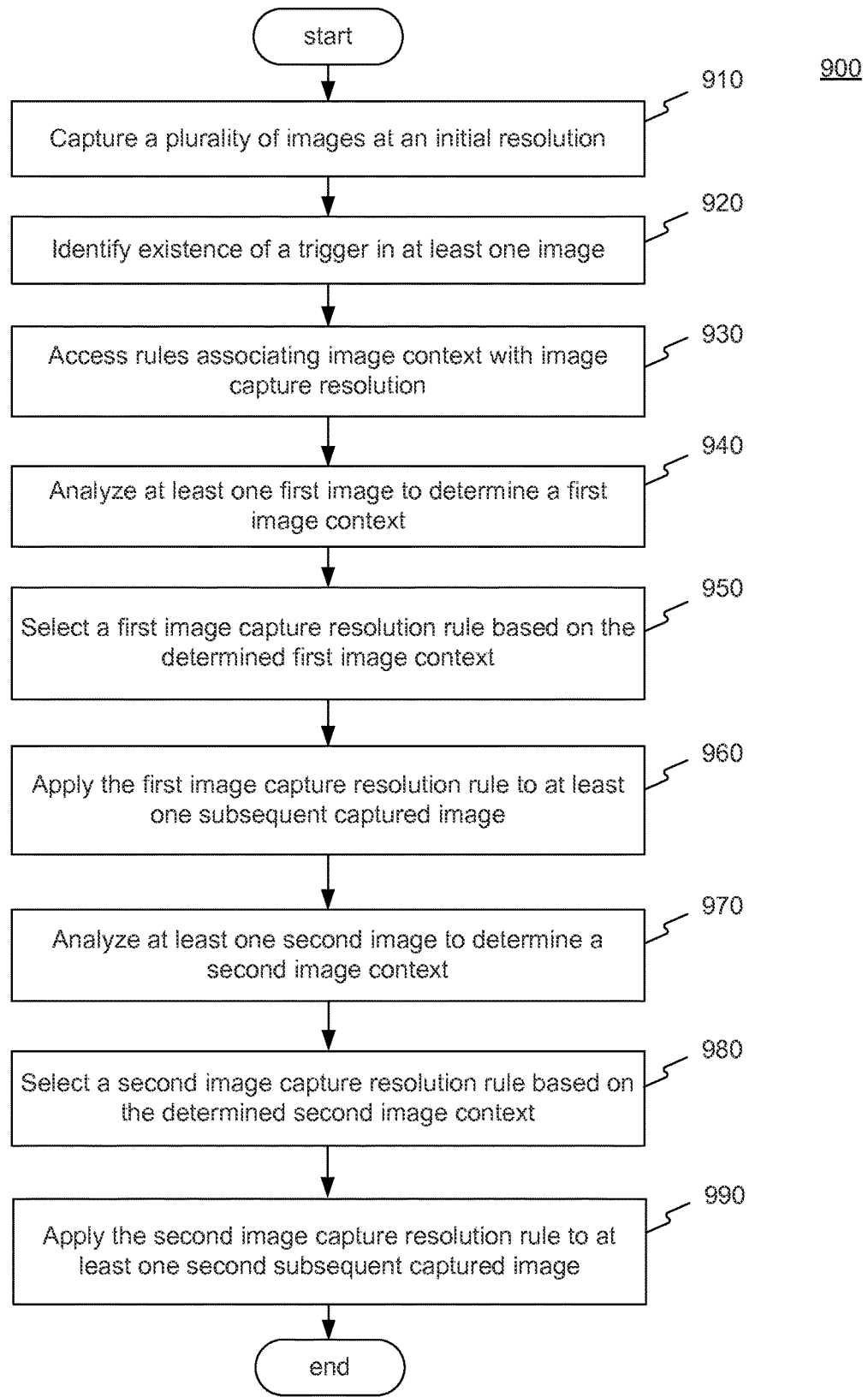

SYSTEMS AND METHODS FOR PROCESSING IMAGES

CROSS REFERENCE TO RELATED APPLICATIONS

This application claims the benefit of priority of U.S. Provisional Patent Application No. 61/799,649, filed on Mar. 15, 2013, and U.S. Provisional Patent Application No. 61/830,122, filed on Jun. 2, 2013, both of which incorporated herein by reference in their entirety.

BACKGROUND

I. Technical Field

This disclosure generally relates to devices and methods for providing information to a user. More particularly, this disclosure relates to devices and methods for providing information to a user by processing images captured from the environment of the user.

II. Background Information

Visual acuity is an indication of the clarity or clearness of a person's vision that is commonly measured twenty feet from an object. When measuring visual acuity, the ability of a person to identify black symbols on a white background at twenty feet is compared to the ability of a person with normal eyesight. This comparison can be symbolized by a ratio. For example, a ratio of 20/70 vision means a person located at a distance of twenty feet can see what a person with normal vision can see at seventy feet. A person has low vision if he or she has a visual acuity between 20/70 and 20/200 in the better-seeing eye that cannot be corrected or improved with regular eyeglasses. The prevalence of low vision is about one in a hundred for people in their sixties and rapidly increases to one in five for people in their nineties. Low vision may also depend on the environment. For example, some individuals may be able to see only when there is ample light.

A person may have low vision (also known as visual impairment) for several reasons. Other than eye damage and failure of the brain to receive visual cues sent by the eyes, different medical conditions may cause visual impairment. Medical conditions that may cause visual impairment include Age-related Macular Degeneration (AMD), retinitis pigmentosa, cataract, and diabetic retinopathy.

AMD, which usually affects adults, is caused by damage to the retina that diminishes vision in the center of a person's visual field. The lifetime risk for developing AMD is strongly associated with certain genes. For example, the lifetime risk of developing AMD is 50% for people that have a relative with AMD, versus 12% for people that do not have relatives with AMD.

Retinitis pigmentosa is an inherited, degenerative eye disease that causes severe vision impairment and often blindness. The disease process begins with changes in pigment and damage to the small arteries and blood vessels that supply blood to the retina. There is no cure for retinitis pigmentosa and no known treatment can stop the progressive vision loss caused by the disease.

A cataract is a clouding of the lens inside the eye which leads to a decrease in vision. Over time, a yellow-brown pigment is deposited within the lens and obstructs light from passing and being focused onto the retina at the back of the eye. Biological aging is the most common cause of a cataract, but a wide variety of other risk factors (e.g., excessive tanning, diabetes, prolonged steroid use) can cause a cataract.

Diabetic retinopathy is a systemic disease that affects up to 80% of all patients who have had diabetes for ten years or more. Diabetic retinopathy causes microvascular damage to a blood-retinal barrier in the eye and makes the retinal blood vessels more permeable to fluids.

People with low vision experience difficulties due to lack of visual acuity, field-of-view, color perception, and other visual impairments. These difficulties affect many aspects of everyday life. Persons with low vision may use magnifying glasses to compensate for some aspects of low vision. For example, if the smallest letter a person with 20/100 vision can read is five times larger than the smallest letter that a person with 20120 vision can read, then 5× magnification should make everything that is resolvable to the person with 20/20 vision resolvable to the person with low vision. However, magnifying glasses are expensive and cannot remedy all aspects of low vision. For example, a person with low vision who wears magnifying glasses may still have a difficult time recognizing details from a distance (e.g., people, signboards, traffic lights, etc.). Accordingly, there is a need for other technologies that can assist people who have low vision accomplish everyday activities.

SUMMARY

Embodiments consistent with the present disclosure provide devices and methods for providing information to a user by processing images captured from the environment of the user. The disclosed embodiments may assist persons who have low vision.

In accordance with a disclosed embodiment, an apparatus is provided for processing images. The apparatus includes an image sensor configured to capture real time images at a plurality of resolutions from an environment of a user. The apparatus also includes a mobile power source. The apparatus also includes at least one processor device configured to process, at an initial resolution, a plurality of images from the image sensor to determine existence of a trigger. The at least one processor device is also configured to access rules associating image context with image capture resolution to enable images of a first context to be processed at a lower capture resolution than images of a second context. The at least one processor device is also configured to analyze at least one first image to determine a first image context. The at least one processor device is also configured to select a first image capture resolution rule based on the determined first image context. The first rule defines a first resolution. The at least one processor device is also configured to apply the first image capture resolution rule to at least one subsequent captured image. The at least one processor device is also configured to analyze at least one second image to determine a second image context. The at least one processor device is also configured to select a second image capture resolution rule based on the determined second image context. The second rule defines a second resolution. The at least one processor device is further configured to apply the second image capture resolution rule to at least one second subsequent captured image. The second resolution is greater than the first resolution.

In accordance with another disclosed embodiment, an apparatus is provided for processing images. The apparatus includes an image sensor configured to capture real time images from an environment of a user. The apparatus also includes a mobile power source. The apparatus also includes at least one processor device configured to process, at an initial frame rate, a plurality of images from the image sensor to determine existence of a trigger. The at least one processor device is configured to access rules associating image context with image capture frame rate to enable images of a first context to be processed at a lower frame rate than images of a second context. The at least one processor device is also configured to analyze at least one first image to determine a first image context. The at least one processor device is also configured to select a first image capture frame rate rule based on the determined image context. The first rule defines a first frame rate. The at least one processor device is also configured to apply the first frame rate to at least one subsequent captured image. The at least one processor device is also configured to analyze at least one second image to determine a second image context. The at least one processor device is also configured to select a second image capture frame rate rule based on the determined second image context. The second rule defines a second frame rate. The at least one processor device is further configured to apply the second frame rate to at least one second subsequent captured image. The second frame rate is higher than the first frame rate.

In accordance with yet another disclosed embodiment, a method is provided for processing images. The method includes capturing a plurality of images at an initial resolution from an environment of a user. The method also includes identifying existence of a trigger in at least one image. The method also includes accessing rules associating image context with image capture resolution to enable images of a first context to be processed at a lower capture resolution than images of a second context. The method also includes analyzing at least one first image to determine a first image context. The method also includes selecting a first image capture resolution rule based on the determined first image context. The first rule defines a first resolution. The method also includes applying the first image capture resolution rule to at least one subsequent captured image. The method also includes analyzing at least one second image to determine a second image context. The method also includes selecting a second image capture resolution rule based on the determined second image context. The second rule defines a second resolution. The method further includes applying the second image capture resolution rule to at least one second subsequent captured image. The second resolution is greater than the first resolution.

Consistent with other disclosed embodiments, non-transitory computer-readable storage media may store program instructions, which are executed by at least one processor device and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this disclosure, illustrate various disclosed embodiments. In the drawings:

FIG. 3B is a schematic illustration of the sensory unit shown in FIG. 3A from a third viewpoint;

FIG. 4A is a schematic illustration of an example of a processing unit from a first viewpoint;

FIG. 5A is a block diagram illustrating an example of the components of an apparatus for aiding persons who have low vision according to a first embodiment;

FIG. 9 is a flowchart showing yet another example of a method for processing images.

DETAILED DESCRIPTION

Figure 1:
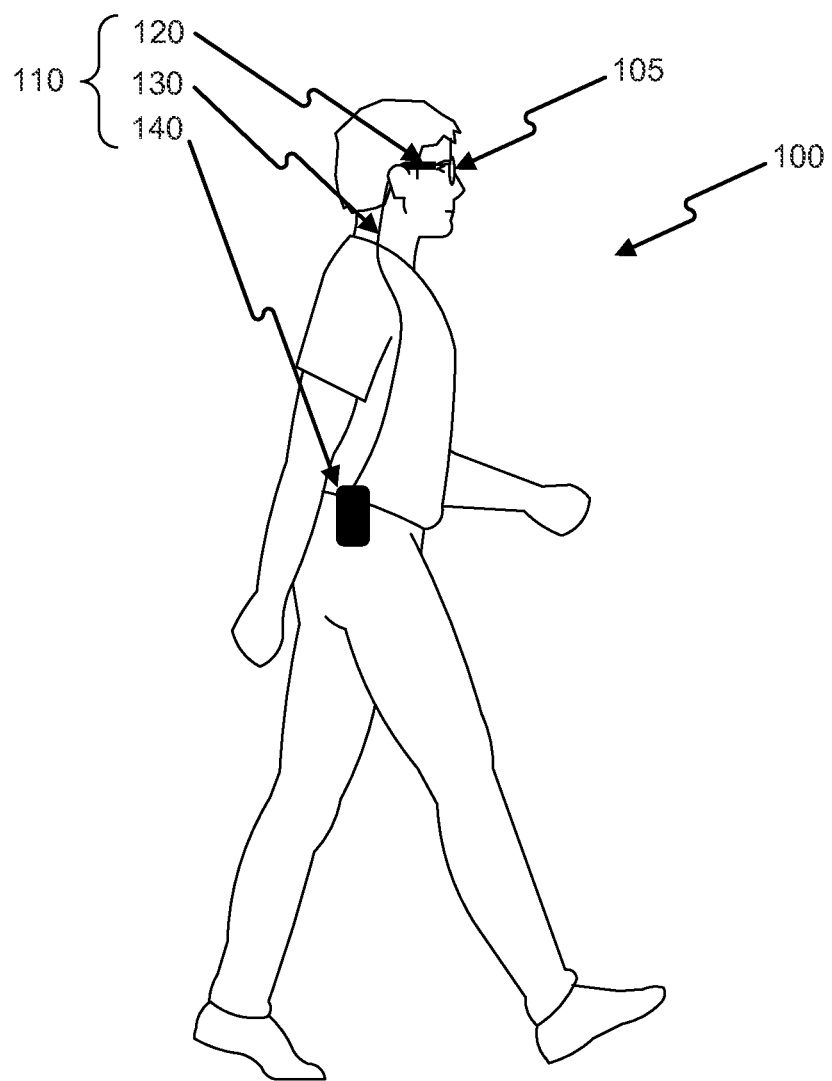
FIG. 1 is a schematic illustration of a user wearing an apparatus for aiding persons who have low vision.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Disclosed embodiments provide devices and methods for assisting people who have low vision. One example of the disclosed embodiments is a device that includes a camera configured to capture real-time image data from the environment of the user. The device also includes a processing unit configured to process the real-time image data and provide real-time feedback to the user. The real-time feedback may include, for example, an output that audibly identifies individuals from a distance, reads signboards, and/or identifies the state of a traffic light.

FIG. 1 illustrates a user 100 wearing an apparatus 110 connected to glasses 105, consistent with a disclosed embodiment. Apparatus 110 may provide functionality for aiding user 100 with various daily activities that are otherwise difficult for user 100 to accomplish due to low vision. Glasses 105 may be prescription glasses, magnifying glasses, non-prescription glasses, safety glasses, sunglasses, etc.

As shown in FIG. 1, apparatus 110 includes a sensory unit 120 and a processing unit 140. Sensory unit 120 may be connected to a support (not shown in FIG. 1) that is mounted on glasses 105. In addition, sensory unit 120 may include an image sensor (not shown in FIG. 1) for capturing real-time image data of the field-of-view of user 100. The term "image data" includes any form of data retrieved from optical signals in the near-infrared, infrared, visible, and ultraviolet spectrums. The image data may be used to form video clips and/or photographs.

Processing unit 140 may communicate wirelessly or via a wire 130 connected to sensory unit 120. In some embodiments, processing unit 140 may produce an output of audible feedback to user 100 (e.g., using a speaker or a bone conduction headphone).

Apparatus 110 is one example of a device capable of implementing the functionality of the disclosed embodiments. Other devices capable of implementing the disclosed embodiments include, for example, a mobile computer with a camera (e.g., a smartphone, a smartwatch, a tablet, etc.) or a clip-on-camera configured to communicate with a processing unit (e.g., a smartphone or a dedicated processing unit, which can be carried in a pocket). A person skilled in the art will appreciate that different types of devices and arrangements of devices may implement the functionality of the disclosed embodiments.

Figure 2A:
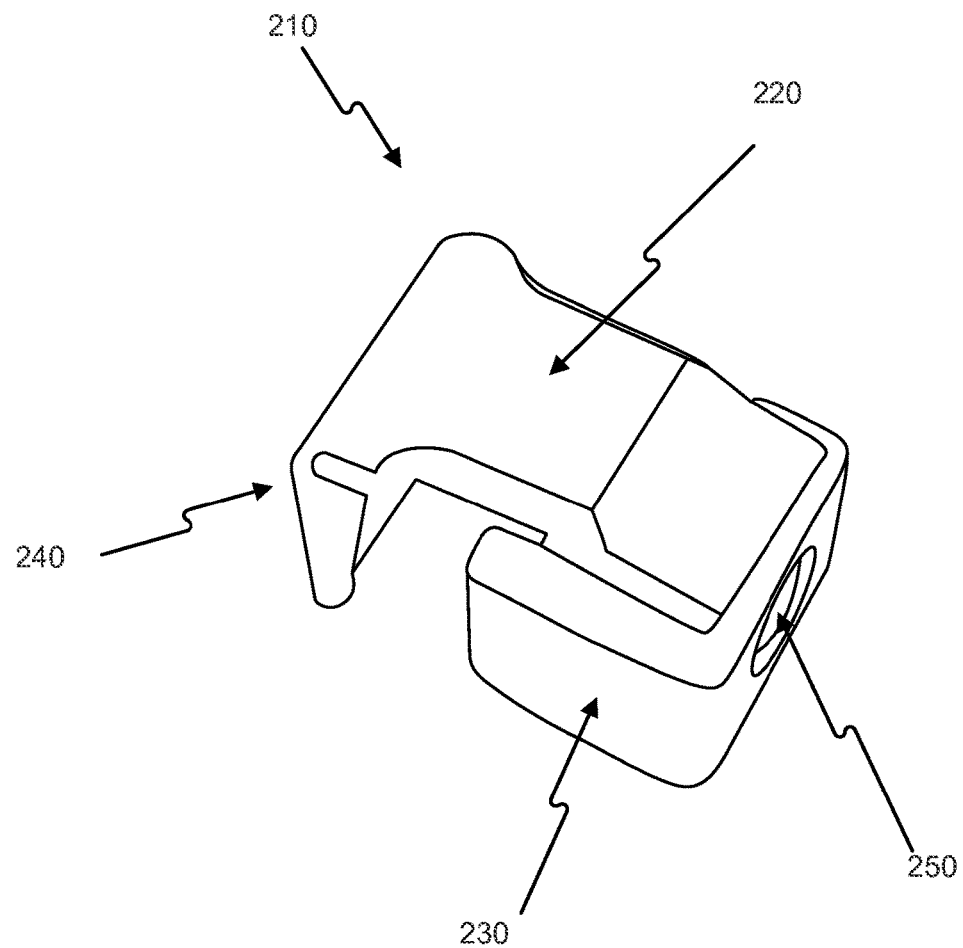
FIG. 2A is a schematic illustration of an example of a support from a first viewpoint.

FIG. 2A is a schematic illustration of an example of a support 210. As discussed in connection with FIG. 1, support 210 may be mounted on glasses 105 and connect to sensory unit 120. The term "support" includes any device or structure that enables detaching and reattaching of a device including a camera to a pair of glasses or to another object (e.g., a helmet). Support 210 may be made from plastic (e.g., polycarbonate), metal (e.g., aluminum), or a combination of plastic and metal (e.g., carbon fiber graphite). Support 210 may be mounted on glasses 105 using screws, bolts, snaps, or any fastening means used in the art.

As shown in FIG. 2A, support 210 includes a base 230 connected to a clamp 240. A bridge 220 connects base 230 with clamp 240. Base 230 and clamp 240 enable sensory unit 120 to easily attach to and detach from support 210. In one embodiment, base 230 may include an internally threaded member 250 for cooperating with a screw (not shown in FIG. 2A) to mount support 210 on glasses 105.

Figure 2B:
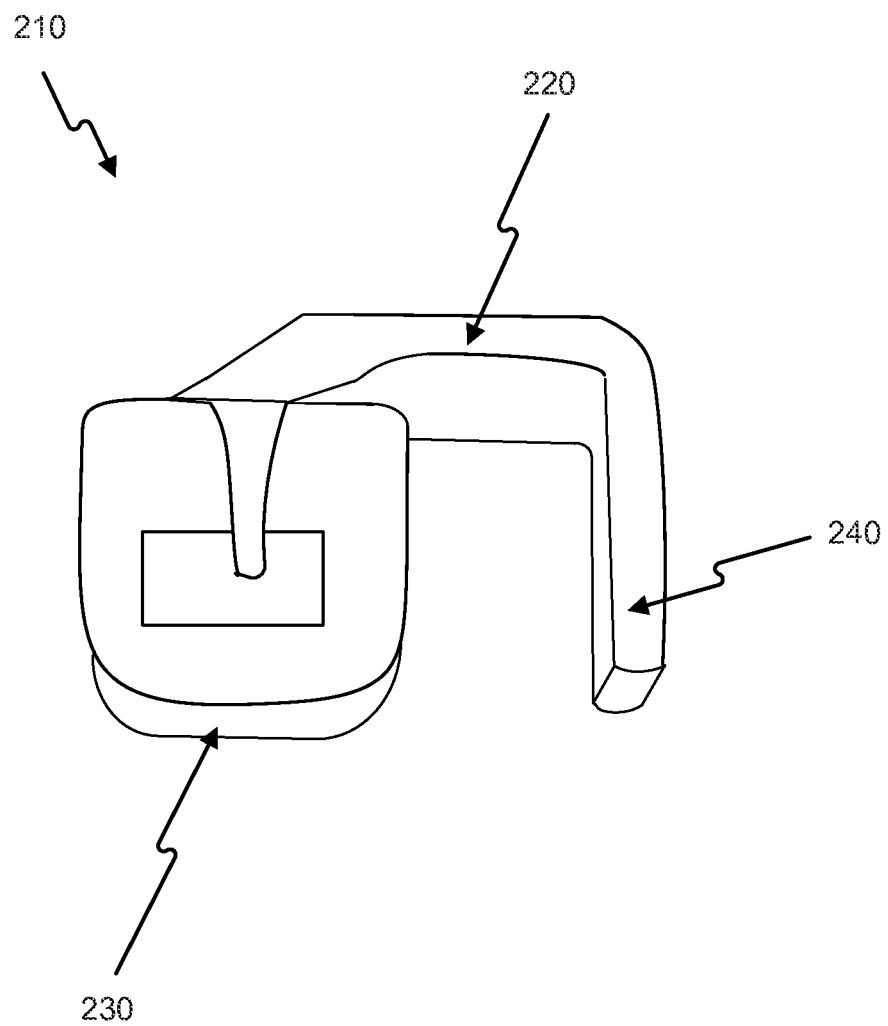
FIG. 2B is a schematic illustration of the support shown in FIG. 2A from a second viewpoint.

FIG. 2B illustrates support 210 from a second viewpoint. The viewpoint shown in FIG. 2B is from a side orientation of support 210.

Figure 2C:
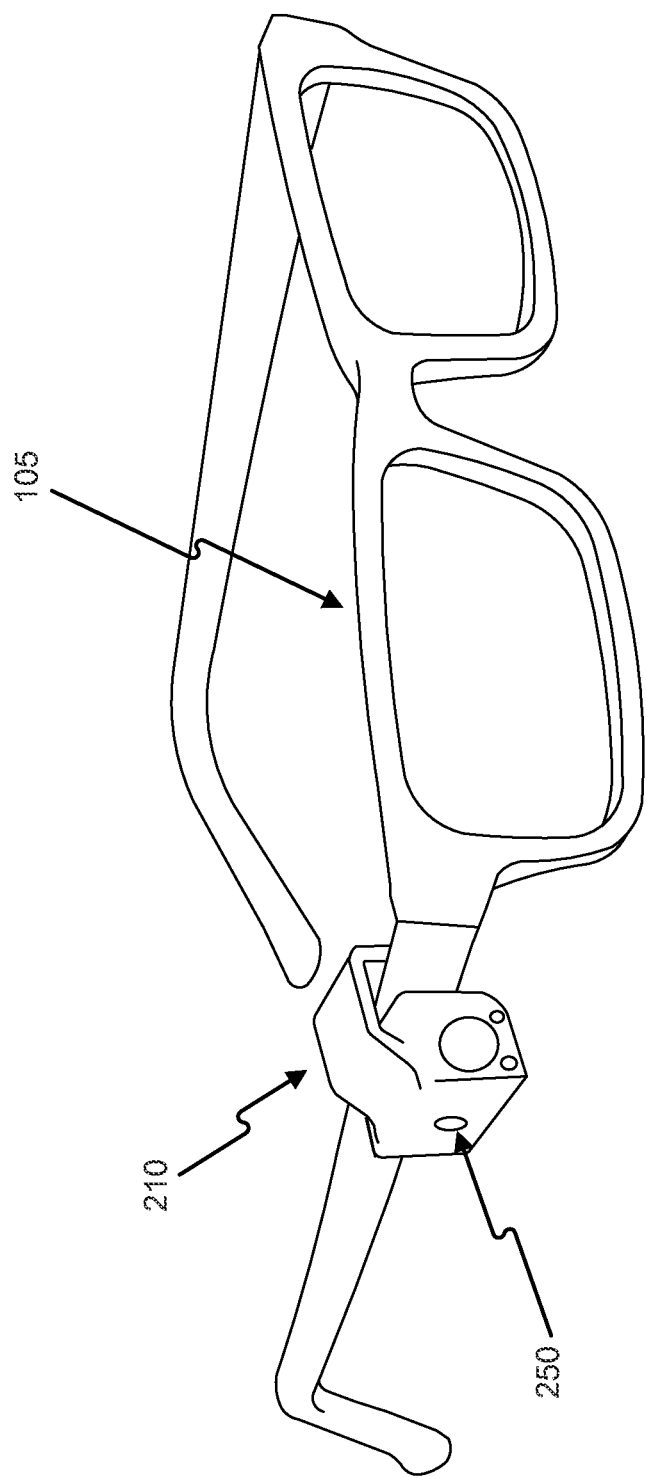
FIG. 2C is a schematic illustration of the support shown in FIG. 2A mounted on a pair of glasses.

FIG. 2C illustrates support 210 mounted on glasses 105. Support 210 may be configured for mounting on any kind of glasses (e.g., eyeglasses, sunglasses, 3D glasses, safety glasses, etc.). As shown in FIG. 2C, sensory unit 120 is not attached to support 210 and, accordingly, support 210 may be sold separately from apparatus 110. This arrangement makes apparatus 110 compatible with a variety of glasses. For example, some users may have several pairs of glasses and may wish to mount a support on each pair of glasses.

In other embodiments, support 210 may be an integral part of a pair of glasses, or sold and installed by an optometrist. For example, support 210 may be configured for mounting on the arms of glasses 105 near the frame front, but before the hinge. Alternatively, support 210 may be configured for mounting on the bridge of glasses 105.

Figure 2D:
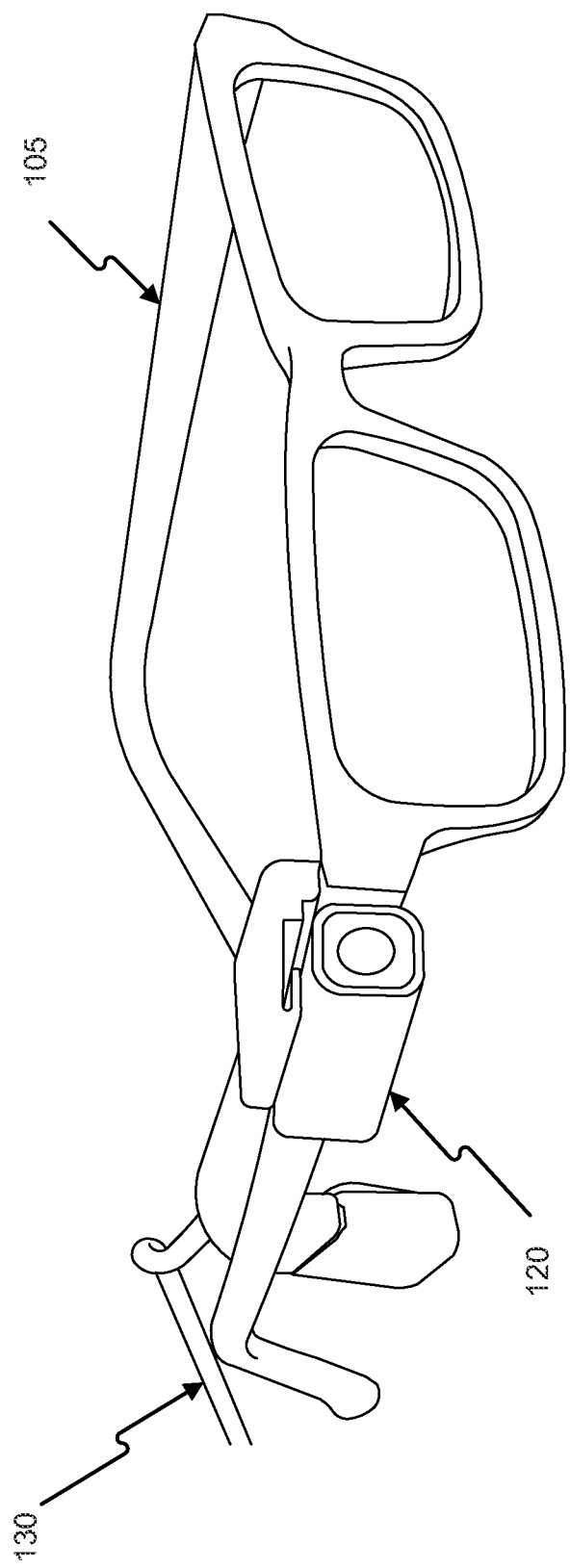
FIG. 2D is a schematic illustration of a sensory unit attached to the support that is mounted on the pair of glasses shown in FIG. 2C.

FIG. 2D illustrates sensory unit 120 attached to support 210 (not visible in FIG. 2D) and support 210 mounted on glasses 105. In some embodiments, support 210 may include a quick release mechanism for disengaging and reengaging sensory unit 120. For example, support 210 and sensory unit 120 may include magnetic elements. As an alternative example, support 210 may include a male latch member and sensory unit 120 may include a female receptacle.

When sensory unit 120 is attached (or reattached) to support 210, the field-of-view of a camera associated with sensory unit 120 may be substantially identical to the field-of-view of user 100. Accordingly, in some embodiments, after support 210 is attached to sensory unit 120, directional calibration of sensory unit 120 may not be required because sensory unit 120 aligns with the field-of-view of user 100.

In other embodiments, support 210 may include an adjustment component (not shown in FIG. 2D) to enable calibration of the aiming direction of sensory unit 120 in a substantially set position that is customized to user 100 wearing glasses 105. For example, the adjustment component may include an adjustable hinge to enable vertical and horizontal alignment of the aiming direction of sensory unit 120. Adjusting the alignment of sensory unit 120 may assist users who have a unique and individual visual impairment. The adjustment may be internal or external to sensory unit 120.

Figure 2E:
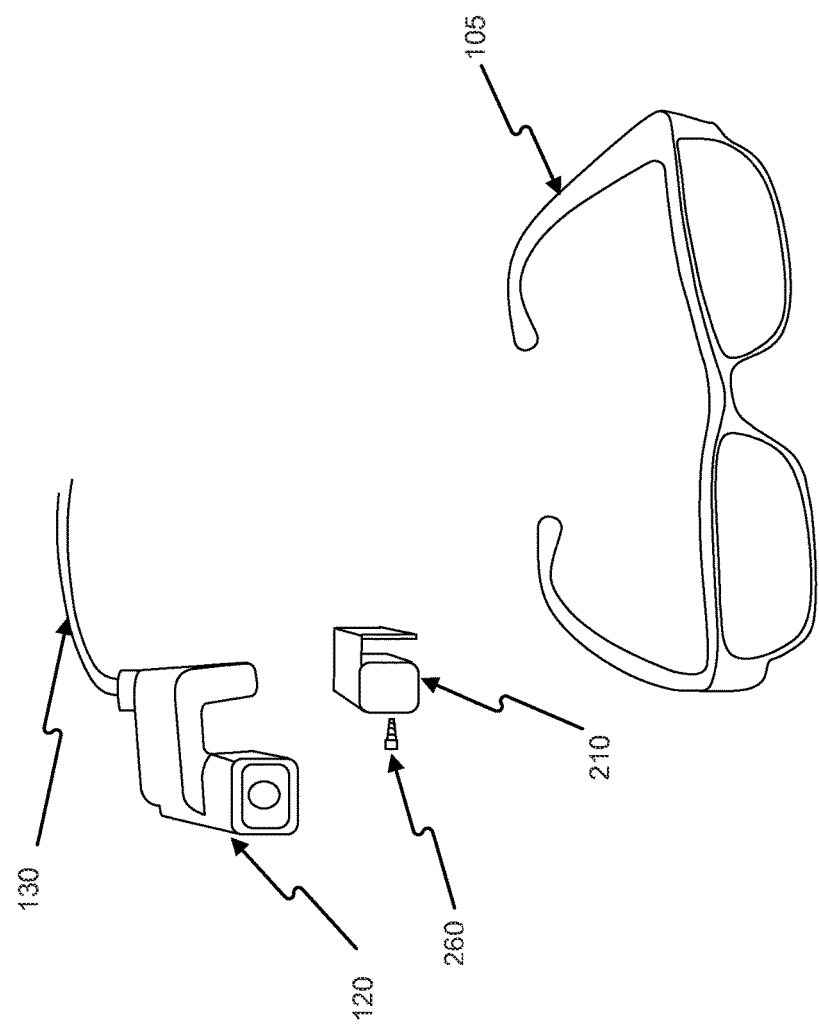
FIG. 2E is an exploded view of FIG. 2D.

FIG. 2E is an exploded view of the components shown in FIG. 2D. Sensory unit 120 may be attached to glasses 105 in the following way. Initially, support 210 may be mounted on glasses 105 using screw 260. Next, screw 260 may be inserted into internally threaded member 250 (not shown in FIG. 2E) in the side of support 210. Sensory unit 120 may then be clipped on support 210 such that it is aligned with the field-of-view of user 100.

Figure 3A:
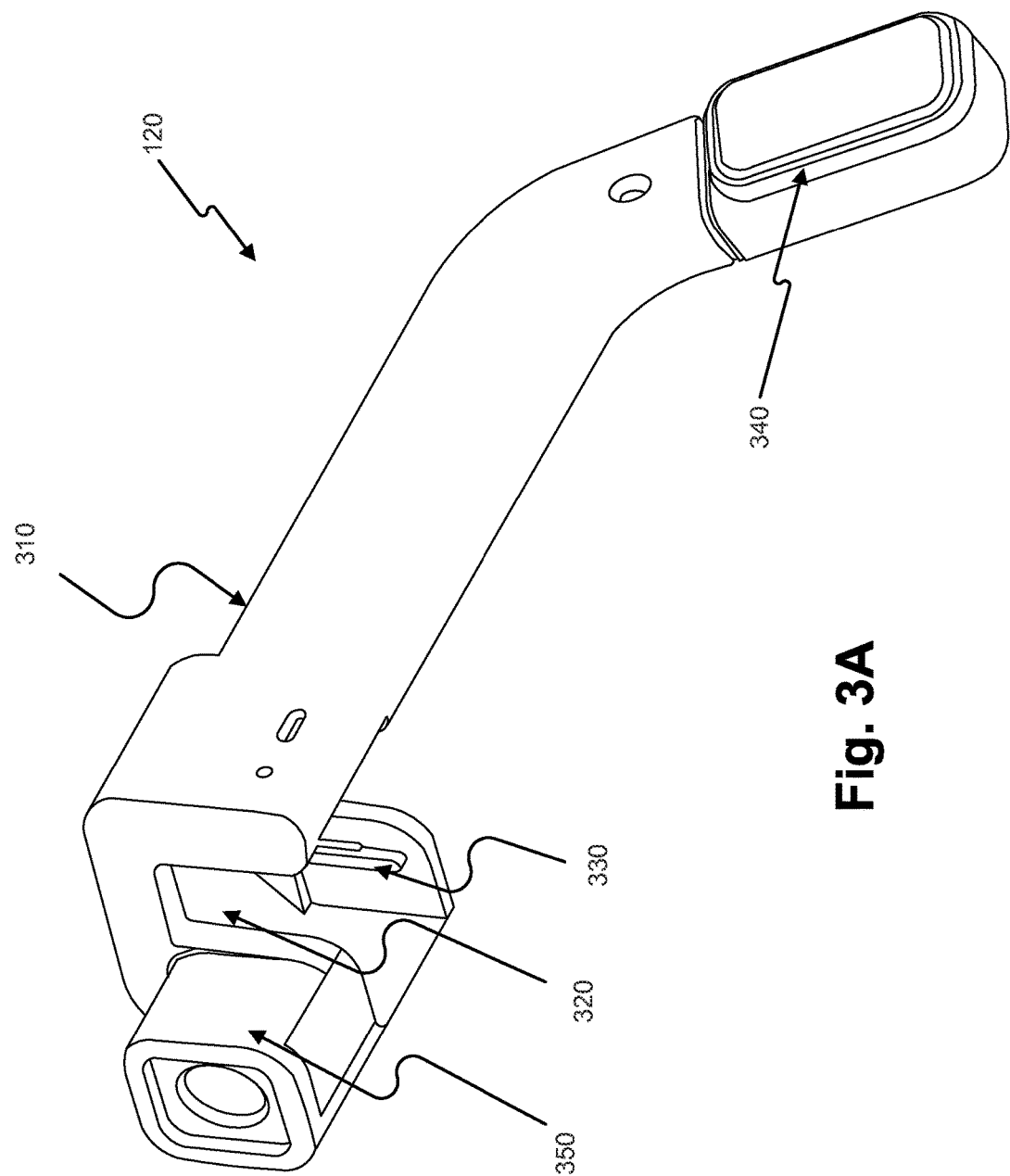
FIG. 3A is a schematic illustration of an example of a sensory unit from a first viewpoint.

FIG. 3A is a schematic illustration of sensory unit 120 from a first viewpoint. As shown in FIG. 3A, sensory unit 120 includes a feedback-outputting unit 340 and an image sensor 350.

Sensory unit 120 is configured to cooperate with support 210 using clip 330 and groove 320, which fits the dimensions of support 210. The term "sensory unit" refers to any electronic device configured to capture real-time images and provide a non-visual output. Furthermore, as discussed above, sensory unit 120 includes feedback-outputting unit 340. The term "feedback-outputting unit" includes any device configured to provide information to a user.

In some embodiments, feedback-outputting unit 340 may be configured to be used by blind persons and persons with low vision. Accordingly, feedback-outputting unit 340 may be configured to output nonvisual feedback. The term "feedback" refers to any output or information provided in response to processing at least one image in an environment. For example, feedback may include a descriptor of a branded product, an audible tone, a tactile response, and/or information previously recorded by user 100. Furthermore, feedback-outputting unit 340 may comprise appropriate components for outputting acoustical and tactile feedback that people with low vision can interpret. For example, feedback-outputting unit 340 may comprise audio headphones, a speaker, a bone conduction headphone, interfaces that provide tactile cues, vibrotactile stimulators, etc.

As discussed above, sensory unit 120 includes image sensor 350. The term "image sensor" refers to a device capable of detecting and converting optical signals in the near-infrared, infrared, visible, and ultraviolet spectrums into electrical signals. The electric signals may be used to form an image based on the detected signal. For example, image sensor 350 may be part of a camera. In some embodiments, when sensory unit 120 is attached to support 210, image sensor 350 may acquire a set aiming direction without the need for directional calibration. The set aiming direction of image sensor 350 may substantially coincide with the field-of-view of user 100 wearing glasses 105. For example, a camera associated with image sensor 350 may be installed within sensory unit 120 in a predetermined angle in a position facing slightly downwards (e.g., 5-15 degrees from the horizon). Accordingly, the set aiming direction of image sensor 350 may match the field-of-view of user 100.

As shown in FIG. 3A, feedback-outputting unit 340 and image sensor 350 are included in a housing 310. The term "housing" refers to any structure that at least partially covers, protects, or encloses a sensory unit. The housing may be made from one or more different materials (e.g., plastic or aluminum). In one embodiment, housing 310 may be designed to engage with a specific pair of glasses having a specific support (e.g., support 210). In an alternative embodiment, housing 310 may be designed to engage more than one pair of glasses, each having a support (e.g., support 210) mounted thereon. Housing 310 may include a connector for receiving power from an external mobile-power-source or an internal mobile-power-source, and for providing an electrical connection to image sensor 350.

Figure 3B:
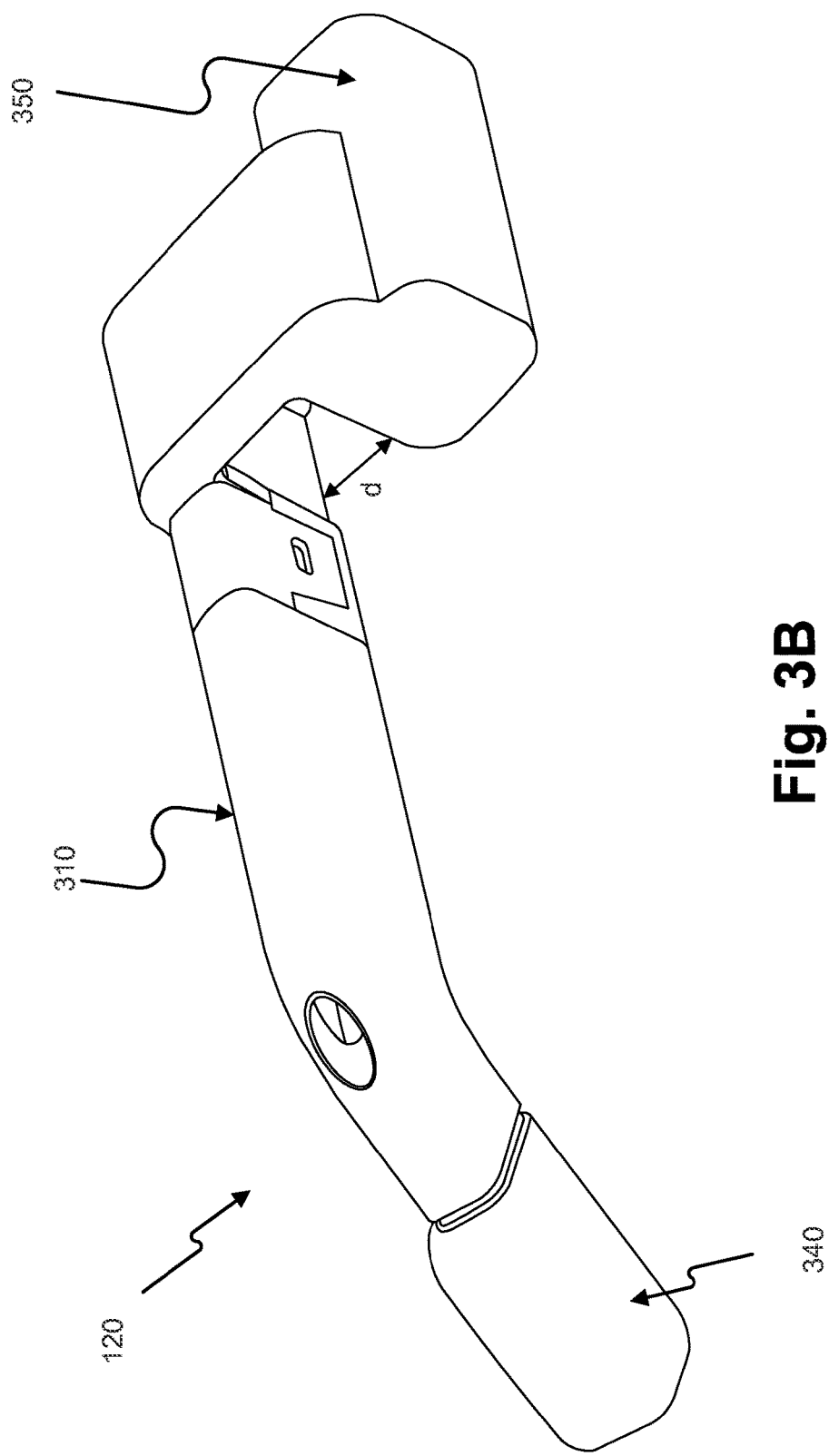
FIG. 3B is a schematic illustration of the sensory unit shown in FIG. 3A from a second viewpoint.

FIG. 3B is a schematic illustration of sensory unit 120 from a second viewpoint. As shown in FIG. 3B, housing 310 includes a U-shaped element. An inner distance "d" between each side of the U-shaped element is larger than the width of the arm of glasses 105. Additionally, the inner distance "d" between each side of the U-shaped element is substantially equal to a width of support 210. The inner distance "d" between each side of the U-shaped element may allow user 100 to easily attach housing 310 to support 210, which may be mounted on glasses 105. As illustrated in FIG. 3B, image sensor 350 is located on one side of the U-shaped element and feedback-outputting unit 340 is located on another side of the U-shaped element.

Figure 3C:
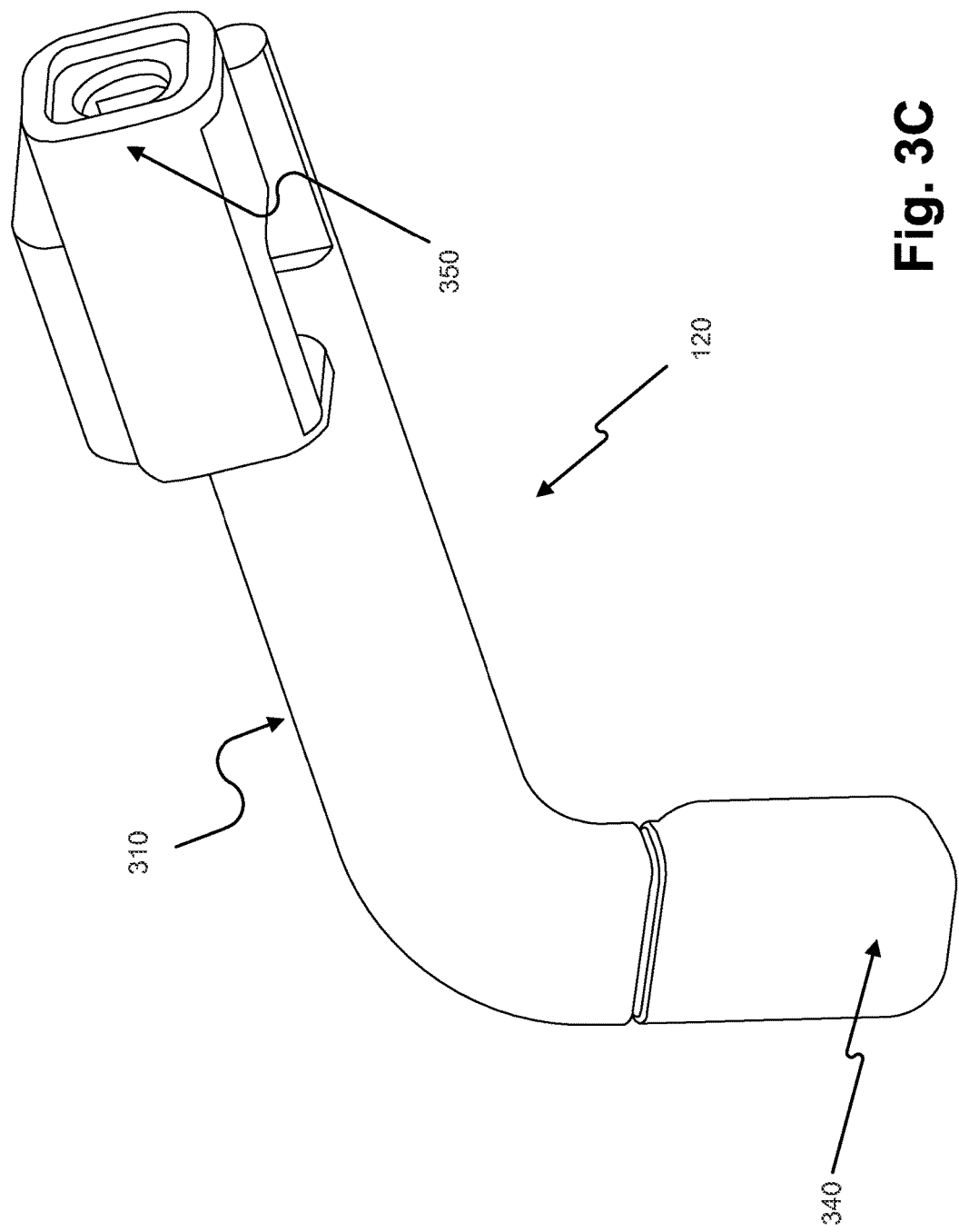
FIG. 3D is a schematic illustration of the sensory unit shown in FIG. 3A from a fourth viewpoint.
FIG. 3E is a schematic illustration of the sensory unit shown in FIG. 3A in an extended position.

FIG. 3C is a schematic illustration of sensory unit 120 from a third viewpoint. The viewpoint shown in FIG. 3C is from a side orientation of sensory unit 120 and shows the side of the U-shaped element that includes image sensor 350.

Figure 3D:
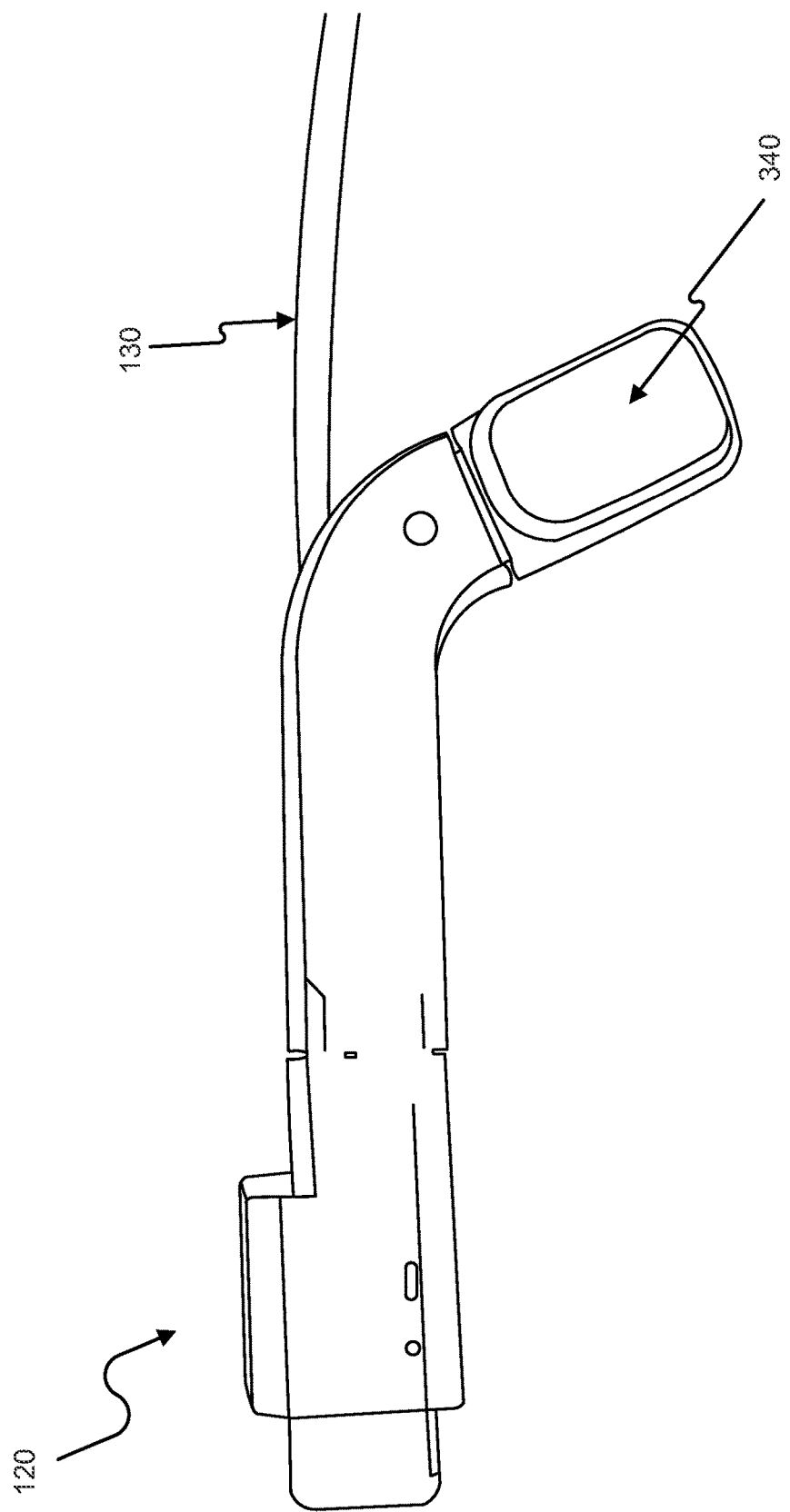

FIG. 3D is a schematic illustration of sensory unit 120 from a fourth viewpoint. The viewpoint shown in FIG. 3D is from an opposite side of the orientation shown in FIG. 3O. FIG. 3D shows the side of the U-shaped element that includes feedback-outputting unit 340.

Figure 3E:
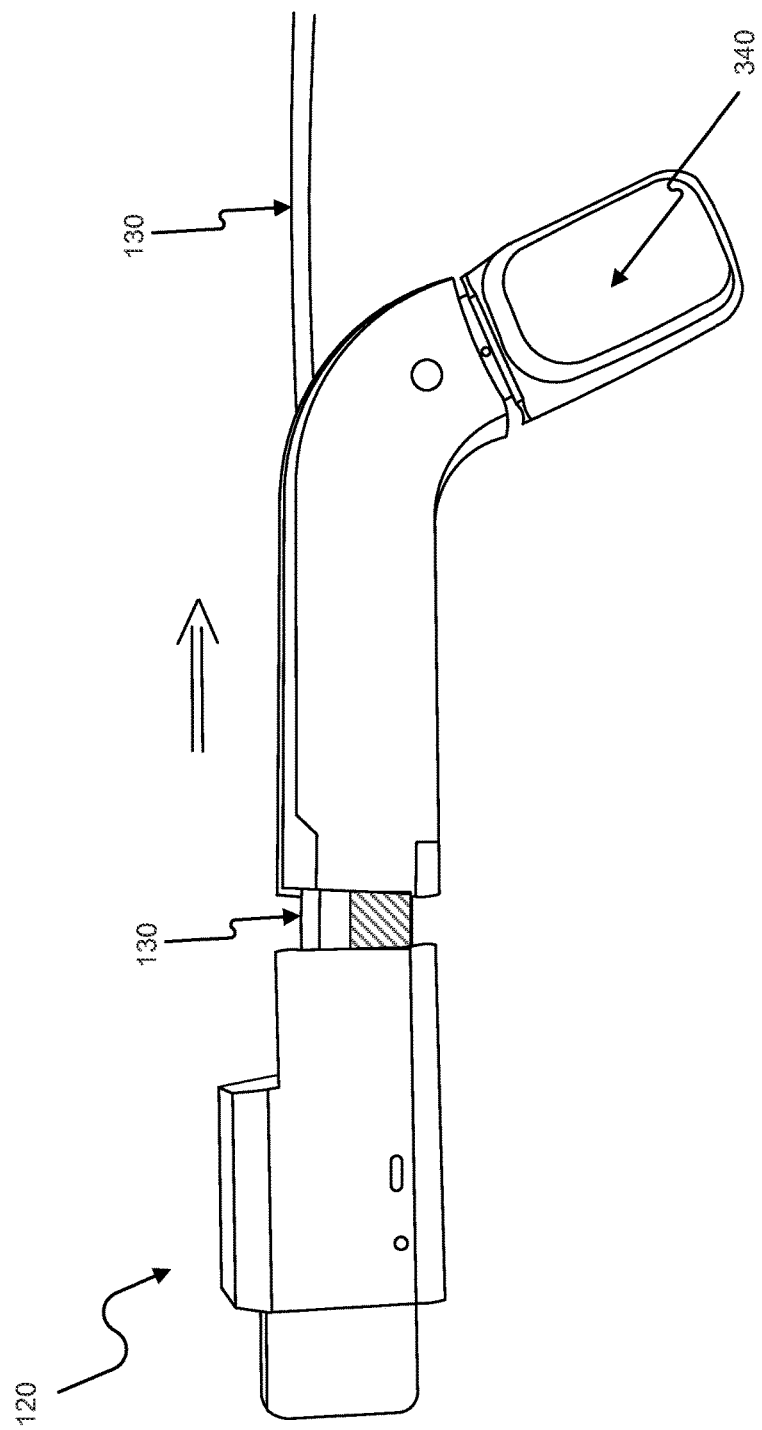

FIG. 3E is a schematic illustration of the sensory unit shown in FIG. 3A in an extended position. As shown in FIG. 3E, a portion of sensory unit 120 is extendable and wire 130 may pass through a channel of sensory unit 120. This arrangement may allow a user to adjust the length and the angle of sensory unit 120 without interfering with the operation of apparatus 110.

User 100 may adjust the U-shaped element of sensory unit 120 so that feedback-outputting unit 340 is positioned adjacent to the user's ear or the user's temple. Accordingly, sensory unit 120 may be adjusted for use with different users who may have different head sizes. Alternatively, a portion of sensory unit 120 may be flexible such that the angle of feedback-outputting unit 340 is relative to the user's ear or the user's temple.

FIG. 4A is a schematic illustration of processing unit 140. As shown in FIG. 4A, processing unit 140 has a rectangular shape, which easily fits in a pocket of user 100. Processing unit 140 includes a connector 400 for connecting wire 130 to processing unit 140. Wire 130 may be used to transmit power from processing unit 140 to sensory unit 120, and data to and from processing unit 140 to sensory unit 120. Alternatively, wire 130 may comprise multiple wires (e.g., a wire dedicated to power transmission and a wire dedicated to data transmission).

Processing unit 140 includes a function button 410 for enabling user 100 to provide input to apparatus 110. Function button 410 may accept different types of tactile input (e.g., a tap, a click, a double-click, a long press, a right-to-left slide, a left-to-right slide). In some embodiments, each type of input may be associated with a different action. For example, a tap may be associated with the function of confirming an action, while a right-to-left slide may be associated with the function of repeating the last output.

Figure 4B:
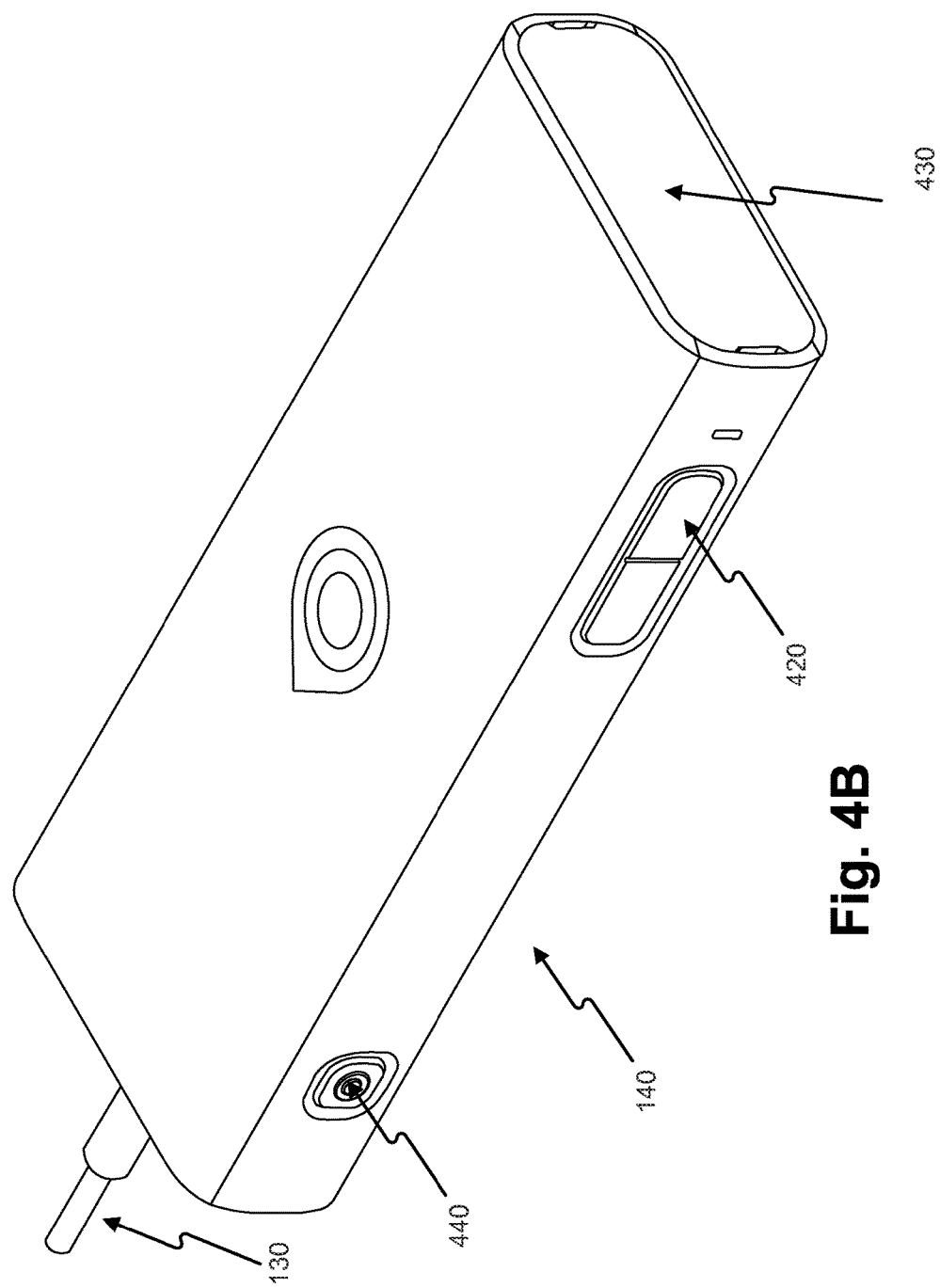
FIG. 4B is a schematic illustration of the processing unit shown in FIG. 4A from a second viewpoint.

FIG. 4B is a schematic illustration of processing unit 140 from a second viewpoint. As shown in FIG. 4B, processing unit 140 includes a volume switch 420, a battery pack compartment 430, and a power port 440. In one embodiment, user 100 may charge apparatus 110 using a charger connectable to power port 440. Alternatively, user 100 may replace a battery pack (not shown) stored in battery pack compartment 430.

FIG. 5A is a block diagram illustrating the components of apparatus 110 according to a first embodiment. Specifically, FIG. 5A depicts an embodiment in which apparatus 110 comprises sensory unit 120 and processing unit 140, as discussed in connection with, for example, FIG. 1. Furthermore, sensory unit 120 may be physically coupled to support 210.

As shown in FIG. 5A, sensory unit 120 includes feedback-outputting unit 340 and image sensor 350. Although one image sensor is depicted in FIG. 5A, sensory unit 120 may include a plurality of image sensors (e.g., two image sensors). For example, in an arrangement with more than one image sensor, each of the image sensors may be face a different direction or be associated with a different camera (e.g., a wide angle camera, a narrow angle camera, an IR camera, etc.). In other embodiments (not shown in the figure) sensory unit 120 may also include buttons and other sensors such as a microphone and inertial measurements devices.

As further shown in FIG. 5A, sensory unit 120 is connected to processing unit 140 via wire 130. Processing unit 140 includes a mobile power source 510, a memory 520, a wireless transceiver 530, and a processor 540.

Processor 540 may constitute any physical device having an electric circuit that performs a logic operation on input or inputs. For example, processor 540 may include one or more integrated circuits, microchips, microcontrollers, microprocessors, all or part of a central processing unit (CPU), graphics processing unit (GPU), digital signal processor (DSP), field-programmable gate array (FPGA), or other circuits suitable for executing instructions or performing logic operations. The instructions executed by processor 540 may, for example, be pre-loaded into a memory integrated with or embedded into processor 540 or may be stored in a separate memory (e.g., memory 520). Memory 520 may comprise a Random Access Memory (RAM), a Read-Only Memory (ROM), a hard disk, an optical disk, a magnetic medium, a flash memory, other permanent, fixed, or volatile memory, or any other mechanism capable of storing instructions.

Although one processor is shown in FIG. 5A, processing unit 140 may include more than one processor. Each processor may have a similar construction or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact.

In some embodiments, processor 540 may change the aiming direction of image sensor 350 using image data provided from image sensor 350. For example, processor 540 may recognize that a user is reading a book and determine that the aiming direction of image sensor 350 is offset from the text. That is, because the words in the beginning of each line of text are not fully in view, processor 540 may determine that image sensor 350 is tilted down and to the right. Responsive thereto, processor 540 may adjust the aiming direction of image sensor 350.

Processor 540 may access memory 520. Memory 520 may be configured to store information specific to user 100. For example, data for image representations of known individuals, favorite products, personal items, etc., may be stored in memory 520. In one embodiment, user 100 may have more than one pair of glasses, with each pair of glasses having support 210 mounted thereon. Accordingly, memory 520 may store information (e.g., personal settings) associated with each pair of glasses. For example, when a user wears his sunglasses may have different preferences than when the user wears reading glasses.

As shown in FIG. 5A, processing unit 140 includes mobile power source 510. Mobile power source 510 may be configured to power processing unit 140 and/or sensory unit 120. The term "mobile power source" includes any device capable of providing electrical power, which can be easily carried by a hand (e.g., the total weight of mobile power source 510 may be less than a pound). Thus, the mobility of the power source enables user 100 to use apparatus 110 in a variety of situations. For example, mobile power source 510 may include one or more batteries (e.g., nickel-cadmium batteries, nickel-metal hydride batteries, and lithium-ion batteries) or any other type of electrical power supply. In some embodiments, mobile power source 510 may be rechargeable and contained within a casing that holds processing unit 140. In other embodiments, mobile power source 510 may include one or more energy harvesting devices for converting ambient energy into electrical energy (e.g., portable solar power units, human vibration units, etc.).

Apparatus 110 may operate in a low-power-consumption mode and in a processing-power-consumption mode. For example, mobile power source 510 can produce five hours of processing-power-consumption mode and fifteen hours of low-power-consumption mode. Accordingly, different power consumption modes may allow mobile power source 510 to produce sufficient power for powering processing unit 140 for various time periods (e.g., more than two hours, more than four hours, more than ten hours, etc.).

Mobile power source 510 may power one or more wireless transceivers (e.g., wireless transceiver 530 in FIG. 5A). The term "wireless transceiver" refers to any device configured to exchange transmissions over an air interface by use of radio frequency, infrared frequency, magnetic field, or electric field. Wireless transceiver 530 may use any known standard to transmit and/or receive data (e.g., Wi-Fi, Bluetooth®, Bluetooth Smart, 802.15.4, or ZigBee). In some embodiments, wireless transceiver 530 may transmit data (e.g., raw image data or audio data) from image sensor 350 to processing unit 140, or wireless transceiver 530 may transmit data from processing unit 140 to feedback-outputting unit 340.

In another embodiment, wireless transceiver 530 may communicate with a different device (e.g., a hearing aid, the user's smartphone, or any wirelessly controlled device) in the environment of user 100. For example, wireless transceiver 530 may communicate with an elevator using a Bluetooth® controller. In such an arrangement, apparatus 110 may recognize that user 100 is approaching an elevator and call the elevator, thereby minimizing wait time. In another example, wireless transceiver 530 may communicate with a smart TV. In such an arrangement, apparatus 110 may recognize that user 100 is watching television and identify specific hand movements as commands for the smart TV (e.g., switching channels). In yet another example, wireless transceiver 530 may communicate with a virtual cane. A virtual cane is any device that uses a laser beam or ultrasound waves to determine the distance from user 100 to an object.

Figure 5B:
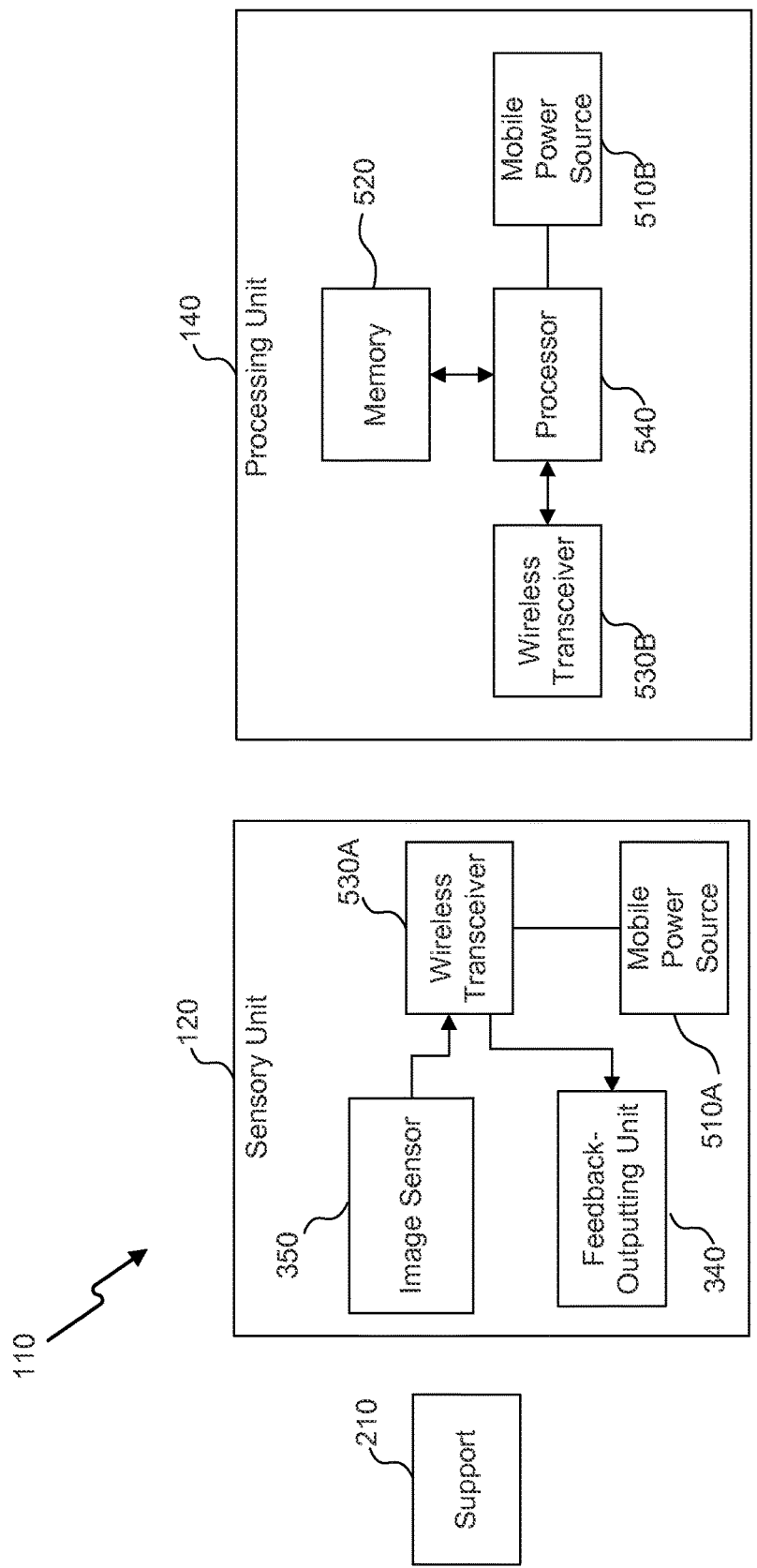
FIG. 5B is a block diagram illustrating an example of the components of an apparatus for aiding persons who have low vision according to a second embodiment.

FIG. 5B is a block diagram illustrating the components of apparatus 110 according to a second embodiment. In FIG. 5B, similar to the arrangement shown in FIG. 5A, support 210 is used to couple sensory unit 120 to a pair of glasses. However, in the embodiment shown in FIG. 5B, sensory unit 120 and processing unit 140 communicate wirelessly. For example, wireless transceiver 530A can transmit image data to processing unit 140 and receive information to be outputted via feedback-outputting unit 340.

In this embodiment, sensory unit 120 includes feedback-outputting unit 340, mobile power source 510A, wireless transceiver 530A, and image sensor 350. Mobile power source 51 OA is contained within sensory unit 120. As further shown in FIG. 5B, processing unit 140 includes wireless transceiver 530B, processor 540, mobile power source 510B, and memory 520.

Figure 5C:
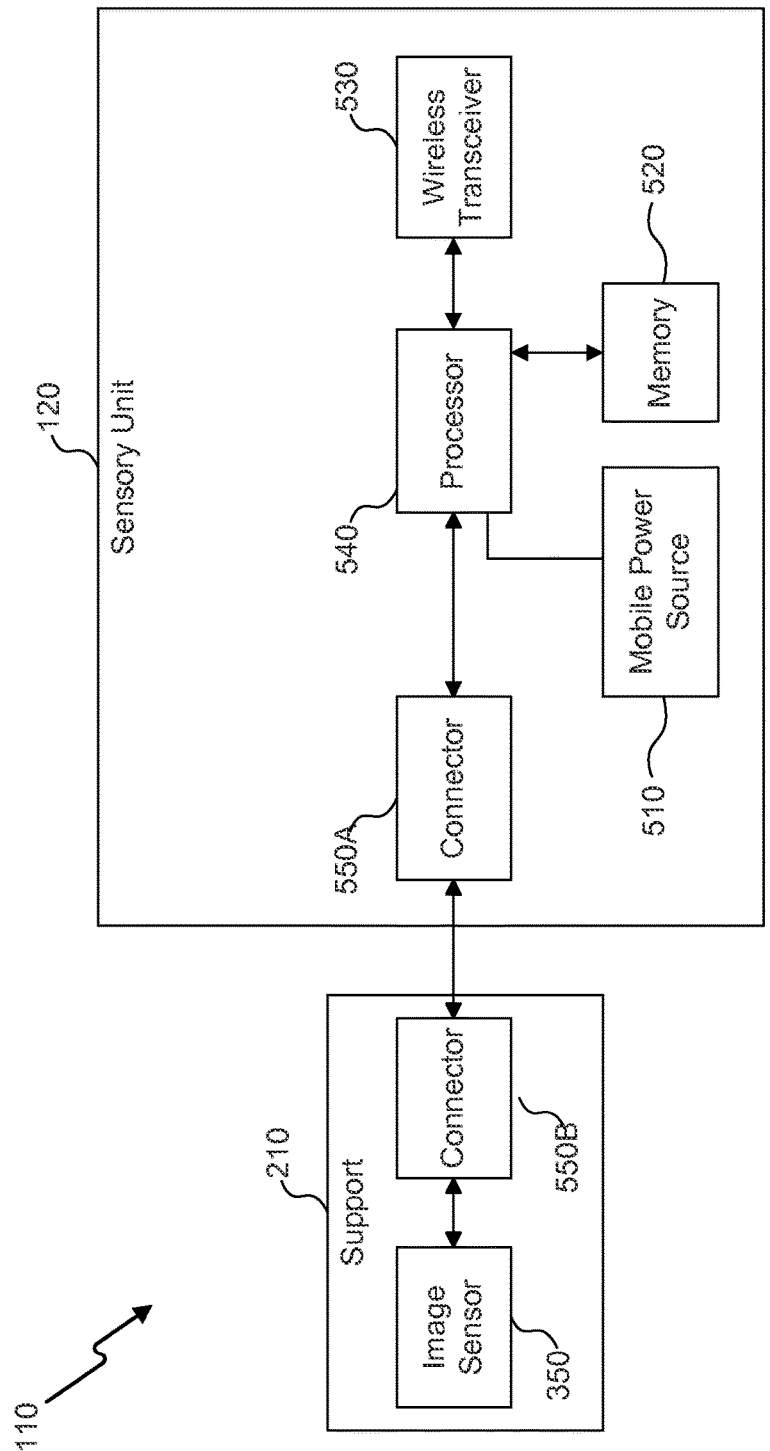
FIG. 5C is a block diagram illustrating an example of the components of an apparatus for aiding persons who have low vision according to a third embodiment.

FIG. 5C is a block diagram illustrating the components of apparatus 110 according to a third embodiment. In particular, FIG. 5C depicts an embodiment in which support 210 includes image sensor 350 and connector 550B. In this embodiment, sensory unit 120 provides functionality for processing data and, therefore, a separate processing unit is not needed in such a configuration.

As shown in FIG. 5C, sensory unit 120 includes processor 540, connector 550A, mobile power source 510, memory 520, and wireless transceiver 530. In this embodiment, apparatus 110 does not include a feedback-outputting unit. Accordingly, wireless transceiver 530 may communicate directly with a hearing aid (e.g., a Bluetooth® hearing aid). In addition, in this embodiment, image sensor 350 is included in support 210. Accordingly, when support 210 is initially mounted on glasses 105, image sensor 350 may acquire a set aiming direction. For example, a camera associated with image sensor 350 may be installed within support 210 in a predetermined angle in a position facing slightly downwards (e.g., 7-12 degrees from the horizon). Furthermore, connector 550A and connector 550B may allow data and power to be transmitted between support 210 and sensory unit 120.

Figure 5D:
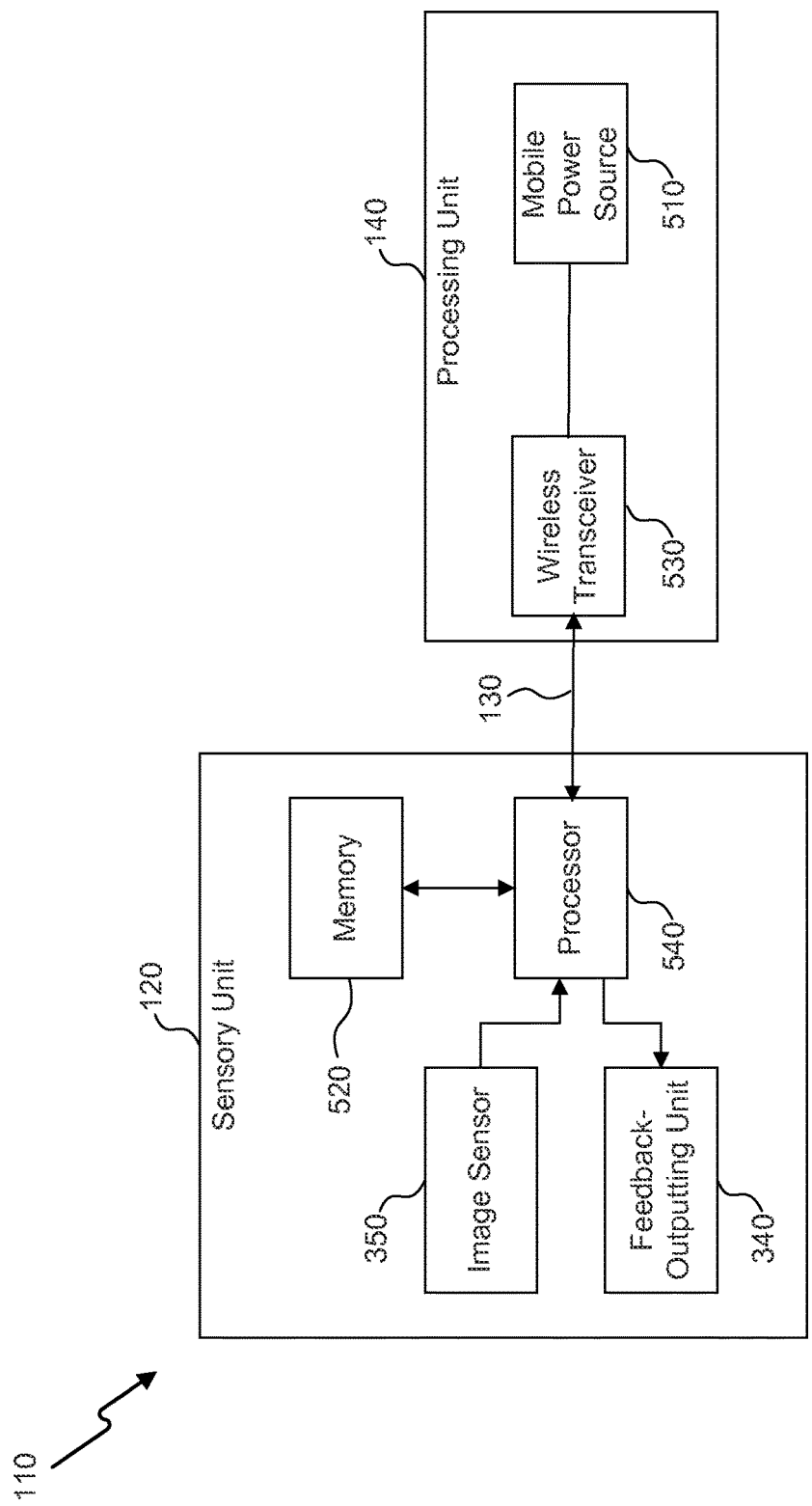
FIG. 5D is a block diagram illustrating an example of the components of an apparatus for aiding persons who have low vision according to a fourth embodiment.

FIG. 5D is a block diagram illustrating the components of apparatus 110 according to a fourth embodiment. In FIG. 5D, sensory unit 120 couples directly to a pair of glasses without the need of a support. In this embodiment, sensory unit 120 includes image sensor 350, feedback-outputting unit 340, processor 540, and memory 520. As shown in FIG. 5D, sensory unit 120 is connected via a wire 130 to processing unit 140. Additionally, in this embodiment, processing unit 140 includes mobile power source 510 and wireless transceiver 530.

As will be appreciated by a person skilled in the art having the benefit of this disclosure, numerous variations and/or modifications may be made to the disclosed embodiments. Not all components are essential for the operation of apparatus 110. Any component may be located in any appropriate part of apparatus 110 and the components may be rearranged into a variety of configurations while providing the functionality of the disclosed embodiments. Therefore, the foregoing configurations are examples and, regardless of the configurations discussed above, apparatus 110 can assist persons who have low vision with their everyday activities in numerous ways.

One way apparatus 110 can assist persons who have low vision is by identifying relevant objects in an environment. For example, in some embodiments, processor 540 may execute one or more computer algorithms and/or signal-processing techniques to find objects relevant to user 100 in image data captured by sensory unit 120. The term "object" refers to any physical object, person, text, or surroundings in an environment.

In one embodiment, apparatus 110 can perform a hierarchical object identification process. In a hierarchical object identification process, apparatus 110 can identify objects from different categories (e.g., spatial guidance, warning of risks, objects to be identified, text to be read, scene identification, and text in the wild) of image data. For example, apparatus 110 can perform a first search in the image data to identify objects from a first category, and after initiating the first search, execute a second search in the image data to identify objects from a second category.

In another embodiment, apparatus 110 can provide information associated with one or more of the objects identified in image data. For example, apparatus 110 can provide information such as the name of an individual standing in front of user 100. The information may be retrieved from a dynamic database stored in memory 520. If the database does not contain specific information associated with the object, apparatus 110 may provide user 100 with nonvisual feedback indicating that a search was made, but the requested information was not found in the database. Alternatively, apparatus 110 may use wireless transceiver 530 to search for and retrieve information associated with the object from a remote database (e.g., over a cellular network or Wi-Fr connection to the Internet).

Another way apparatus 110 can assist persons who have low vision is by performing a continuous action that relates to an object in an environment. A continuous action may involve providing continuous feedback regarding the object. For example, apparatus 110 can provide continuous feedback associated with an object identified within a field-of-view of image sensor 350, and suspend the continuous feedback when the object moves outside the field-of-view of image sensor 350. Examples of continuous feedback may include audibly reading text, playing a media file, etc. In addition, in some embodiments, apparatus 110 may provide continuous feedback to user 100 based on information derived from a discrete image or based on information derived from one or more images captured by sensory unit 120 from the environment of user 100.

Another type of continuous action includes monitoring the state of an object in an environment. For example, in one embodiment, apparatus 110 can track an object as long as the object remains substantially within the field-of-view of image sensor 350. Furthermore, before providing user 100 with feedback, apparatus 110 may determine whether the object is likely to change its state. If apparatus 110 determines that the object is unlikely to change its state, apparatus 110 may provide a first feedback to user 100. For example, if user 100 points to a road sign, apparatus 110 may provide a first feedback that comprises a descriptor of the road sign. However, if apparatus 110 determines that the object is likely to change its state, apparatus 110 may provide a second feedback to user 100 after the object has changed its state. For example, if user 100 points at a traffic light, the first feedback may comprise a descriptor of the current state of the traffic light (e.g., the traffic light is red) and the second feedback may comprise a descriptor indicating that the state of traffic light has changed (i.e., the traffic light is now green).

Apparatus 110 may also determine that an object that is expected to change its state is not functioning and provide appropriate feedback. For example, apparatus 110 may provide a descriptor indicating that a traffic light is broken.

Apparatus 110 can also assist persons who have low vision by making intelligent decisions regarding a person's intentions. Apparatus 110 can make these decisions by understanding the context of a situation. Accordingly, disclosed embodiments may retrieve contextual information from captured image data and adjust the operation of apparatus 110 based on at least the contextual information. The term "contextual information" (or "context") refers to any information having a direct or indirect relationship with an object in an environment. In some embodiments, apparatus 110 may retrieve different types of contextual information from captured image data. One type of contextual information is the time and/or the place that an image of the object was captured. Another example of a type of contextual information is the meaning of text written on the object. Other examples of types of contextual information include the identity of an object, the type of the object, the background of the object, the location of the object in the frame, the physical location of the user relative to the object, etc.

In an embodiment, the type of contextual information that is used to adjust the operation of apparatus 110 may vary based on objects identified in the image data and/or the particular user who wears apparatus 110. For example, when apparatus 110 identifies a package of cookies as an object, apparatus 110 may use the location of the package (i.e., at home or at the grocery store) to determine whether or not to read the list of ingredients aloud. Alternatively, when apparatus 110 identifies a signboard identifying arrival times for trains as an object, the location of the sign may not be relevant, but the time that the image was captured may affect the output. For example, if a train is arriving soon, apparatus 110 may read aloud the information regarding the coming train. Accordingly, apparatus 110 may provide different responses depending on contextual information.

Apparatus 110 may use contextual information to determine a processing action to execute or an image resolution of image sensor 350. For example, after identifying the existence of an object, contextual information may be used to determine if the identity of the object should be announced, if text written on the object should be audibly read, if the state of the object should be monitored, or if an image representation of the object should be saved. In some embodiments, apparatus 110 may monitor a plurality of images and obtain contextual information from specific portions of an environment. For example, motionless portions of an environment may provide background information that can be used to identify moving objects in the foreground.

Yet another way apparatus 110 can assist persons who have low vision is by automatically carrying out processing actions after identifying specific objects and/or hand gestures in the field-of-view of image sensor 350. For example, processor 540 may execute several actions after identifying one or more triggers in image data captured by apparatus 110. The term "trigger" includes any information in the image data that may cause apparatus 110 to execute an action. For example, apparatus 110 may detect as a trigger a finger of user 100 pointing to one or more coins. The detection of this gesture may cause apparatus 110 to calculate a sum of the value of the one or more coins. As another example of a trigger, an appearance of an individual wearing a specific uniform (e.g., a policeman, a fireman, a nurse) in the field-of-view of image sensor 350 may cause apparatus 110 to make an audible indication that this particular individual is nearby.

In some embodiments, the trigger identified in the image data may constitute a hand-related trigger. The term "hand-related trigger" refers to a gesture made by, for example, the user's hand, the user's finger, or any pointed object that user 100 can hold (e.g., a cane, a wand, a stick, a rod, etc.).

In other embodiments, the trigger identified in the image data may include an erratic movement of an object caused by user 100. For example, unusual movement of an object can trigger apparatus 110 to take a picture of the object. In addition, each type of trigger may be associated with a different action. For example, when user 100 points to text, apparatus 110 may audibly read the text. As another example, when user 100 erratically moves an object, apparatus 110 may audibly identify the object or store the representation of that object for later identification.

Apparatus 110 may use the same trigger to execute several actions. For example, when user 100 points to text, apparatus 110 may audibly read the text. As another example, when user 100 points to a traffic light, apparatus 110 may monitor the state of the traffic light. As yet another example, when user 100 points to a branded product, apparatus 110 may audibly identify the branded product. Furthermore, in embodiments in which the same trigger is used for executing several actions, apparatus 110 may determine which action to execute based on contextual information retrieved from the image data. In the examples above, wherein the same trigger (pointing to an object) is used, apparatus 110 may use the type of the object (text, a traffic light, a branded product) to determine which action to execute.

To assist user 100 throughout his or her daily activities, apparatus 100 may follow several procedures for saving processing resources and prolonging battery life. For example, apparatus 110 can use several image resolutions to form images. Higher image resolution provides more detailed images, but requires more processing resources. Lower image resolution provides less detailed images, but saves processing resources. Therefore, to prolong battery life, apparatus 110 may have rules for capturing and processing high resolution image under certain circumstances, and rules for capturing and processing low resolution image when possible. For example, apparatus 110 may capture higher resolution images when performing Optical Character Recognition (OCR), and capture low resolution images when searching for a trigger.

One of the common challenges persons with low vision face on a daily basis is reading. Apparatus 110 can assist persons who have low vision by audibly reading text that is present in user 100 environment. Apparatus 110 may capture an image that includes text using sensory unit 120. After capturing the image, to save resources and to process portions of the text that are relevant to user 100, apparatus 110 may initially perform a layout analysis on the text. The term "layout analysis" refers to any process of identifying regions in an image that includes text. For example, layout analysis may detect paragraphs, blocks, zones, logos, titles, captions, footnotes, etc.

In one embodiment, apparatus 110 can select which parts of the image to process, thereby saving processing resources and battery life. For example, apparatus 110 can perform a layout analysis on image data taken at a resolution of one megapixel to identify specific areas of interest within the text. Subsequently, apparatus 110 can instruct image sensor 350 to capture image data at a resolution of five megapixels to recognize the text in the identified areas. In other embodiments, the layout analysis may include initiating at least a partial OCR process on the text.

In another embodiment, apparatus 110 may detect a trigger that identifies a portion of text that is located a distance from a level break in the text. A level break in the text represents any discontinuity of the text (e.g., a beginning of a sentence, a beginning of a paragraph, a beginning of a page, etc.). Detecting this trigger may cause apparatus 110 to read the text aloud from the level break associated with the trigger. For example, user 100 can point to a specific paragraph in a newspaper and apparatus 110 may audibly read the text from the beginning of the paragraph instead of from the beginning of the page.

In addition, apparatus 110 may identify contextual information associated with text and cause the audible presentation of one portion of the text and exclude other portions of the text. For example, when pointing to a food product, apparatus 110 may audibly identify the calorie value of the food product. In other embodiments, contextual information may enable apparatus 110 to construct a specific feedback based on at least data stored in memory 520. For example, the specific feedback may assist user 100 to fill out a form (e.g., by providing user 100 audible instructions and details relevant to a form in the user's field-of-view).

To improve the audible reading capabilities of apparatus 110, processor 540 may use OCR techniques. The term "optical character recognition" includes any method executable by a processor to retrieve machine-editable text from images of text, pictures, graphics, etc. OCR techniques and other document recognition technology typically use a pattern matching process to compare the parts of an image to sample characters on a pixel-by-pixel basis. This process, however, does not work well when encountering new fonts, and when the image is not sharp. Accordingly, apparatus 110 may use an OCR technique that compares a plurality of sets of image regions that are proximate to each other. Apparatus 110 may recognize characters in the image based on statistics relate to the plurality of the sets of image regions. By using the statistics of the plurality of sets of image regions, apparatus 110 can recognize small font characters defined by more than four pixels e.g., six or more pixels. In addition, apparatus 110 may use several images from different perspectives to recognize text on a curved surface. In another embodiment, apparatus 110 can identify in image data an existence of printed information associated with a system command stored in a database and execute the system command thereafter. Examples of a system command include: "enter training mode," "enter airplane mode," "backup content," "update operating system," etc.

The disclosed OCR techniques may be implemented on various devices and systems and are not limited to use with apparatus 110. For example, the disclosed OCR techniques provide accelerated machine reading of text. In one embodiment, a system is provided for audibly presenting a first part of a text from an image, while recognizing a subsequent part of the text. Accordingly, the subsequent part may be presented immediately upon completion of the presentation of the first part, resulting in a continuous audible presentation of standard text in less than two seconds after initiating OCR.

As is evident from the foregoing, apparatus 110 may provide a wide range of functionality. More specifically, one embodiment consistent with the present disclosure provides an image capturing and processing function that may assist a person with low vision to recognize objects. Apparatus 110 may use the image capturing and processing function to identify objects near the user of apparatus 110. In this way, in situations in which a visually-impaired user of apparatus 110 cannot identify or is unsure of the identity of an object nearby, apparatus 110 may be configured to recognize the object or to process and present the processed image to the user, which may be easier for the visually-impaired user to recognize.

Figure 6:
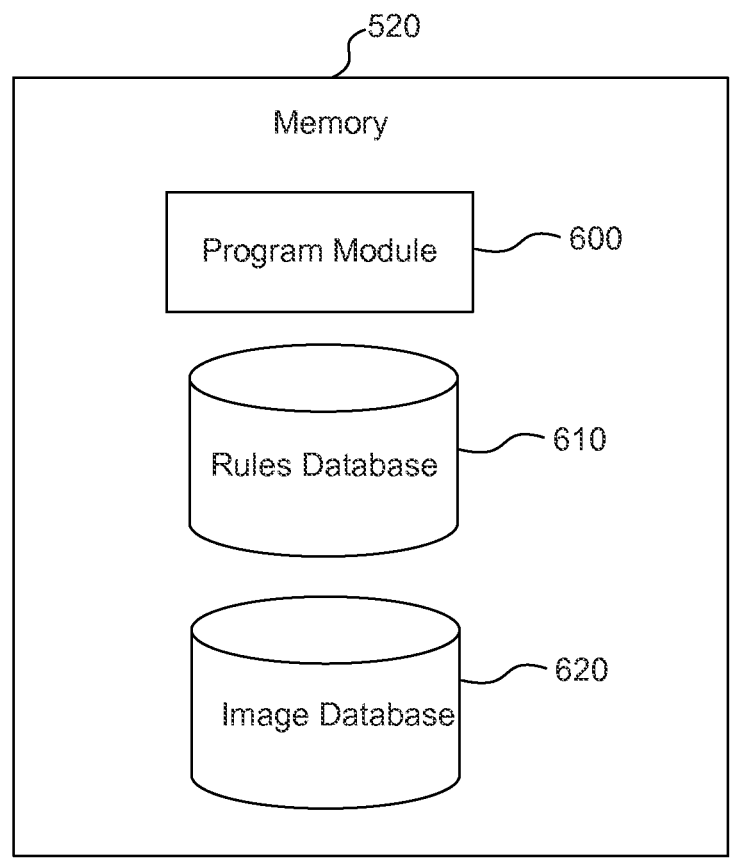
FIG. 6 is a block diagram of a memory that may be used in conjunction with an apparatus for aiding persons who have low vision.

FIG. 6 is a block diagram of memory 520. Memory 520 may include components configured to store various types of data that may be used in image capturing or processing. For example, memory 520 may include at least one program module 600 configured to store program code or instructions that may be executed by processor 540 to perform methods and operations to identify objects near the user of apparatus 110. Memory 520 may also include a rules database 610 configured to store data, such as rules that associate image contexts with image capture resolutions and rules that associate image contexts with image capture frame rates. Memory 520 may also include an image database 620 configured to store data, such as captured images, and information associated with captured images, such as time, place, identification of objects, sizes of images, etc.

Program module 600, rules database 610, and image database 620 may be implemented in software, hardware, firmware, a mix of any of those, or the like. Other components of processing unit 140 and/or sensory unit 120 may be configured to perform processes to implement and facilitate operations of program module 600, rules database 610, and/or image database 620. For example, program module 600, rules database 610, and/or image database 620 may include software, hardware, or firmware instructions (or a combination thereof) executable by one or more processors (e.g., processor 540), alone or in various combinations with each other. Program module 600, rules database 610, and/or image database 620 may be configured to interact with each other and/or other components of apparatus 110 to perform functions consistent with disclosed embodiments. In some embodiments, any of the disclosed modules (e.g., program module 600) may each include dedicated sensors (e.g., IR, image sensors, etc.) and/or dedicated application processing devices to perform the functionality associated with each module.

Rules database 610 and/or image database 620 may include one or more memory devices that store information and are accessed and/or managed through a computing device, such as processing unit 140. In some embodiments, rules database 610 and/or image database 620 may be located in memory 520, as shown in FIG. 6. In other embodiments, database 630 may be located remotely from memory 520, and may be accessible to other components of apparatus 110 (e.g., processing unit 140) via one or more wireless connections (e.g., a wireless network). While one rules database 610 and one image database 620 are shown, it should be understood that several separate and/or interconnected databases may make up rules database 610 and/or image database 620. Rules database 610 and/or image database 620 may include computing components (e.g., database management system, database server, etc.) configured to receive and process requests for data stored in memory devices associated with rules database 610 and/or image database 620 and to provide data from rules database 610 and/or image database 620.

Figure 7:
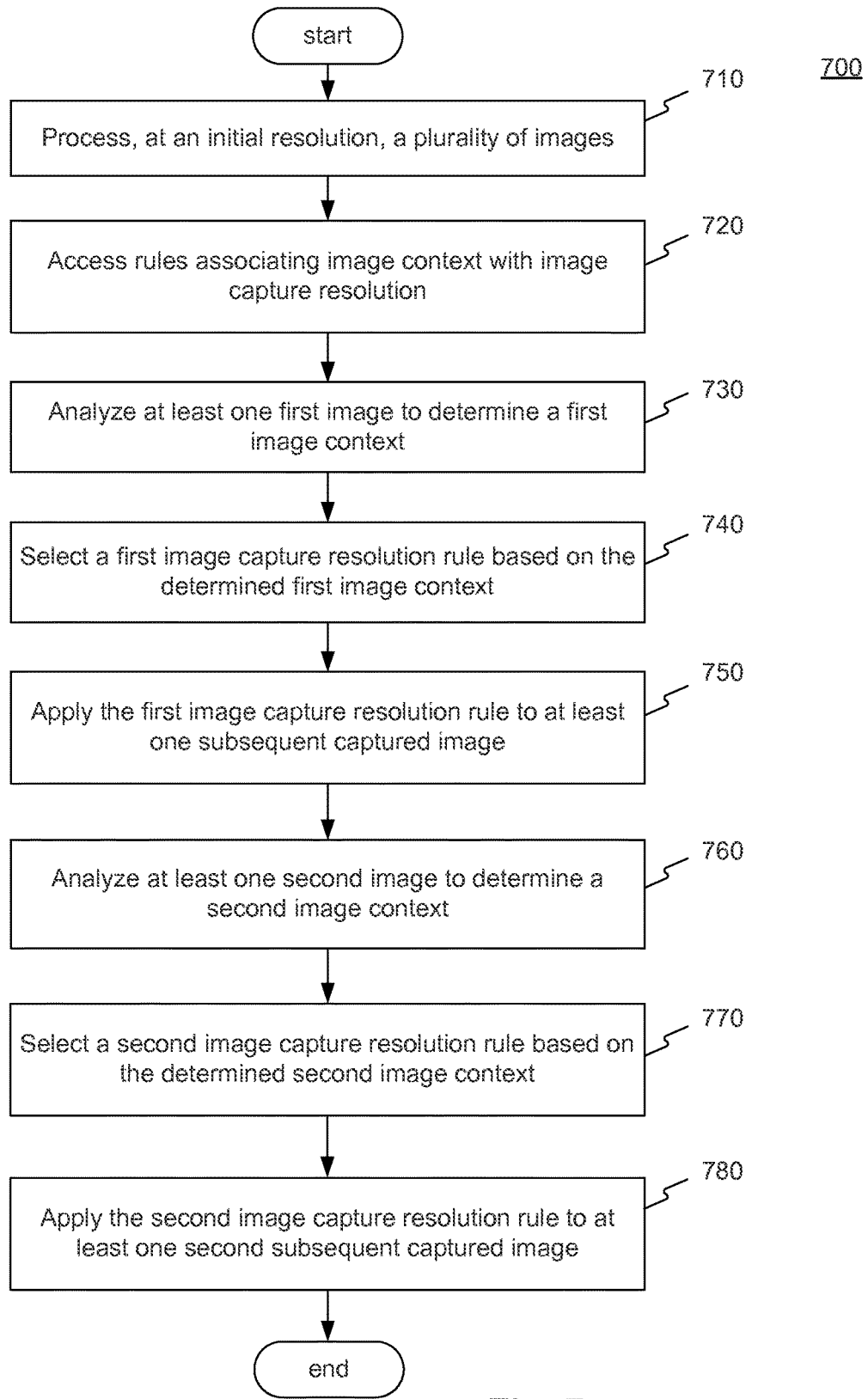
FIG. 7 is a flowchart showing an example of a method for processing images.

FIG. 7 shows an example of a method 700 for processing images, consistent with a disclosed embodiment. Method 700 may include one or more operations that may be performed by processor 540. As shown in FIG. 7, processor 540 may be configured to process, at an initial resolution, a plurality of images from image sensor 350 to determine existence of a trigger (Step 710). The initial resolution may vary depending on specific applications. For example, in one embodiment, the initial resolution may be lower than or higher than 5 megapixels. In another embodiment, the initial resolution may be lower than or higher than 80,000 pixels. The plurality of images may be captured by image sensor 350, and may be received by processor 540 from image sensor 350 for processing. Alternatively or additionally, images captured by image sensor 350 may be stored in memory 520, such as image database 620, and processor 540 may retrieve images from memory 520 for processing. The trigger that is determined in step 710 may be, for example, a gesture made by a user who at least partially appears in the images.

Processor 540 may access rules associating image contexts with image capture resolutions to enable images of a first context to be processed at a lower capture resolution than images of a second context (Step 720). The rules may be referred to as image capture resolution rules. The rules may define resolutions to be used for capturing and/or processing images associated with different image contexts. The image capture resolution rules may be stored in rules database 610 included in memory 520. The term resolution means the fidelity at which the image data is captured. For example, this includes the number of picture elements ("pixels"), the frequency of taking images, zoom configuration, and sensor sensitivity parameters (such as gain and aperture), and other operational aspects of sensory unit 120.

An image context may provide information associated with the context of a particular image. For example, an image context may be related to the time and/or place that an image of an object and/or an environment was captured. As other examples, an image context may be related to the meaning of text written on an object that appears in an image. As another example, context may be related to a particular arrangement of objects in the image. Certain image contexts may be associated with different rules. For example, the rules may specify a low image capture resolution for images associated with certain image contexts. Processor 540 may analyze the scene to determine that an object was inserted into the field of view and optimize the capture parameters to capture that object, possibly at the expense of other objects. The image capture resolution rules may specify a high capture resolution for images associated with other image contexts.

Processor 540 may analyze at least one first image to determine a first image context (Step 730). For example, processor 540 may analyze at least one first image to determine the time and/or place that the first image was captured. Processor 540 may select a first capture resolution rule based on the determined first image context (Step 740). The first capture resolution rule may define a relatively lower resolution for capturing images associated with the first image context. For example, the first image capture resolution rule may define a first resolution of, e.g., 80,000 pixels, megapixel, 5 megapixels, 10 megapixels, etc. The first resolution may be greater than, lower than, or substantially equal to the initial resolution. For example, in some embodiments, the first resolution may be greater than 300,000 pixels, and the initial resolution may be equal to the first resolution. In some embodiments, the first resolution may be greater than 10 megapixels, and the initial resolution may be less than 1 megapixel. In other embodiments, the first resolution may be 1 megapixel, and the initial resolution may be 2 megapixels. Furthermore, in some embodiments, the first image capture resolution rule may include zoom information. Zoom information may include, for example, 1×, 2×, 8×, or 16× zoom, which was used in capturing the images, or which will be used in capturing subsequent images.

Processor 540 may apply the first image capture resolution rule to at least one subsequent captured image (Step 750). For example, processor 540 may apply a first resolution of 10 megapixels to one or more images captured following the first image (e.g., the third and fourth subsequent captured images). In some embodiments, the first image capture resolution rule may further define a plurality of image portions. Each image portion may be associated with a different resolution to be captured in the at least one subsequent captured image. For example, the first image capture resolution rule may define a first image portion, a second image portion, and a third image portion. The first image portion may be captured at a resolution of 1 megapixel in a first subsequent captured image. The second image portion may be captured at a resolution of 1.5 megapixels in a second subsequent captured image. The third image portion may be captured at a resolution of 2 megapixels in a third subsequent captured image.

The first, second, and third image portions may be portions of the same image. Alternatively, the first, second, and third image portions may be portions of different images. For example, the first image portion may be a portion of a first subsequent captured image, and the second and third image portions may be portions of a second subsequent captured image. In some embodiments, at least one image portion defined by the first image capture resolution rule may not be part of the at least one subsequent captured image. For example, the first image portion may be a portion of the first image (which is not one of the subsequent captured images), and other image portions may be portions of a separate image, such as one of the subsequent captured images. Thus, processor 540 may process portions of images across multiple images.

Processor 540 may analyze at least one second image to determine a second image context (Step 760). For example, the second image context may be related to the meaning of text written on an object captured in an image. Processor 540 may select a second image capture resolution rule based on the determined second image context (Step 770). For example, the second image capture resolution rule may define a second resolution of, e.g., 80,000 pixels, 1 megapixel, 5 megapixels, 10 megapixels, or 15 megapixels, etc., for capturing images. The second resolution may be greater than, lower than, or substantially equal to the first resolution. For example, the second resolution may be 2 megapixels, and the first resolution may be 2 megapixels, less than 2 megapixels, or greater than 2 megapixels. Processor 540 may apply the second image capture resolution rule to at least one second subsequent captured image (Step 780). For example, processor 540 may apply a 2 megapixels resolution to one or more images captured following the second image, such as the fourth and fifth images captured following the second image.

Processor 540 may be further configured to perform other operations that may be included in method 700. For example, processor 540 may be further configured to execute an action selected from multiple context-based actions. The multiple context-based actions may include at least one action associated with a first resolution and at least one additional action associated with a second resolution. For example, the at least one action associated with the first resolution may include an action of recognizing a place in which the image was captured using the first resolution. The at least one additional action associated with the second resolution may include an action of recognizing the meaning of text written on an object using the second resolution. Thus, an action selected from the multiple context-based actions may be an action that includes both recognizing a place and recognizing the meaning of text, for example, from the same image. Processor 540 may be further configured to identify objects in images that were captured in the second resolution. For example, processor 540 may identify buildings, vehicles, landmarks, human beings from images captured in the second resolution. Processor 540 may be further configured to execute an optical character recognition operation on images captured in the second resolution, for example, to identify text written on a surface.

Figure 8:
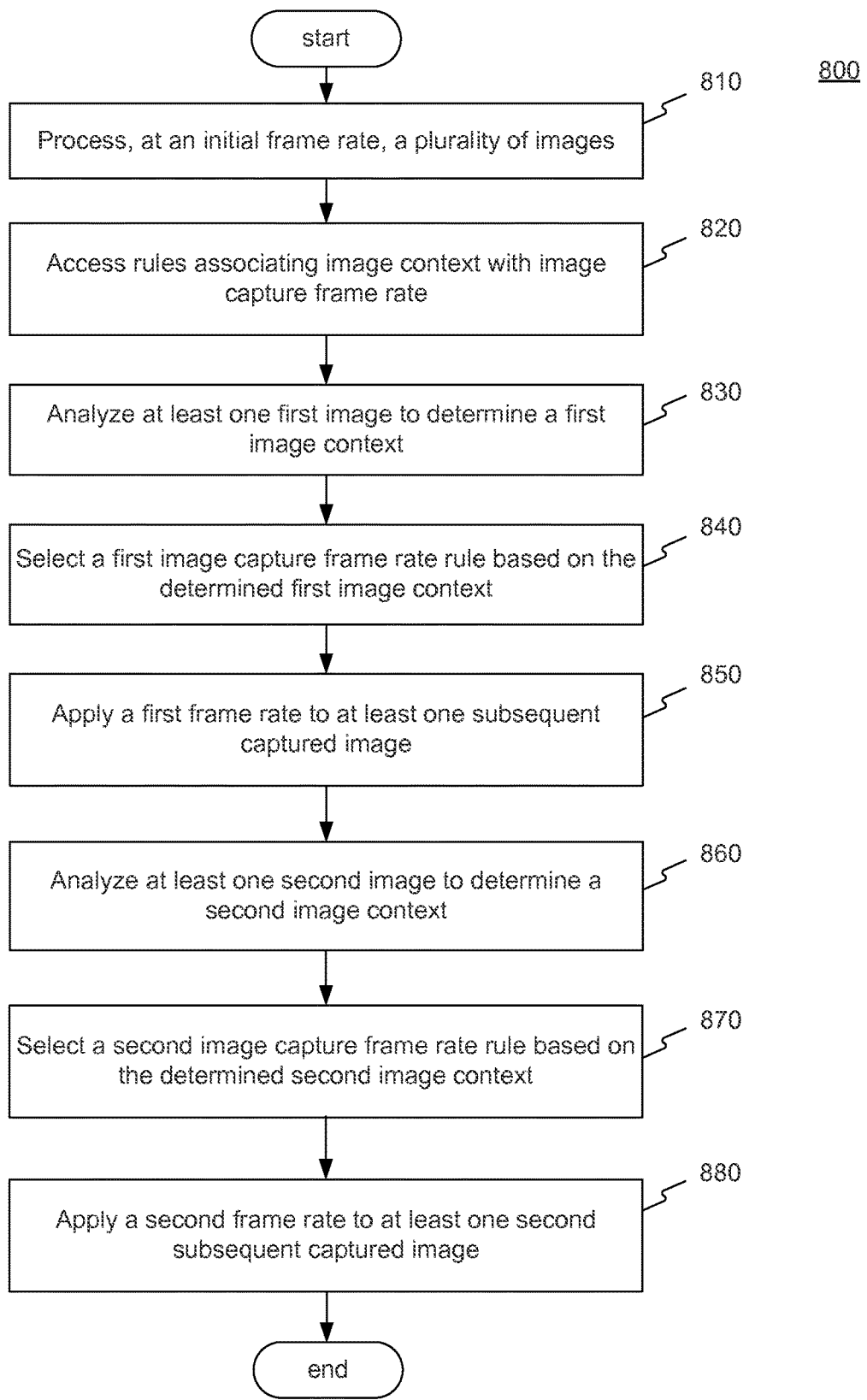
FIG. 8 is a flowchart showing another example of a method for processing images.

FIG. 8 is a flowchart showing an example of a method 800 for processing images, consistent with a disclosed embodiment. Method 800 may include a plurality of operations that may be performed by processor 540. Processor 540 may be configured to process, at an initial frame rate, a plurality of images from image sensor 350 to determine existence of a trigger (Step 810). Processor 540 may access rules associating image context with image capture frame rates to enable images of a first context to be processed at a lower frame rate than images of a second context (Step 820). The rules may define frame rates to be used for capturing images. Processor 540 may analyze at least one first image to determine a first image context (Step 830). For example, the first image context may be related to the time and/or place that an image of an object was captured.

Processor 540 may select a first image capture frame rate rule based on the determined image context (Step 840). The first image capture frame rate rule may define a first frame rate (e.g., 1 frame-per-second). Processor 540 may apply the first frame rate to at least one subsequent captured image (Step 850). For example, processor may apply a 1 frame-per-second frame rate to the second, third, and fourth subsequent captured images. Processor 540 may analyze at least one second image to determine a second image context (Step 860). For example, the second image context may be related to the meaning of text written on an object in the at least one second image. Processor 540 may select a second image capture frame rate rule based on the determined second image context (Step 870). The second image capture frame rate rule may define a second frame rate, for example, 2 frames-per-second. Processor 540 may apply the second frame rate to at least one second subsequent captured image (Step 880). For example, processor 540 may apply the 2-frames-per-second frame rate to the fifth, sixth, and seventh subsequent captured images. The second frame rate may be higher than, lower than, or equal to the first frame rate. For example, the second frame rate may be 2-framesper-second, and the first frame rate may be 2-frames-per-second, higher than 2-frames-per-second, or lower than 2-frames-per-second.

The initial frame rate may be associated with an image resolution, and the second frame rate may be associated with a different image resolution. For example, the initial frame rate may be associated with an image resolution of 1 megapixel, and the second frame rate may be associated with an image resolution of 2 megapixels. The first frame rate may be higher than, lower than, or substantially equal to the initial frame rate. For example, the initial frame rate may be less than 10 frames-per-second, and the first frame rate may be higher than 9 frames-per-second, lower than 10-frames-per-second, or equal to the initial frame rate. In some embodiments, the first frame rate may be higher than 29 frames-per-second.

FIG. 9 is a flowchart showing a method 900 for processing images, consistent with a disclosed embodiment. Method 900 may include a plurality of operations that may be performed by processor 540. For example, processor 540 may capture a plurality of images at an initial resolution from an environment of a user (Step 910). In one embodiment, processor 540 may control image sensor 350 to capture the images. Processor 540 may identify the existence of a trigger in at least one image (Step 920). For example, processor 540 may identify as a trigger a gesture made by a user who appears in a captured image. Processor 540 may access rules associating image contexts with image capture resolutions to enable images of a first context to be processed at a lower capture resolution than images of a second context (Step 930). For example, processor 540 may access rules that define a lower capture resolution of 80,000 pixels for processing images of a first context, and a higher capture resolution of 2 megapixels for processing images of a second context. Processor 540 may analyze at least one first image to determine a first image context (Step 940). For example, processor 540 may analyze the first captured image to determine the place the first image was captured. Processor 540 may be configured to select a first image capture resolution rule based on the determined first image context (Step 950). The first rule may define a first resolution; for example, 1 megapixel for processing images.

Processor 540 may apply the first image capture resolution rule to at least one subsequent captured image (Step 960). For example, processor 540 may apply a first image capture resolution rule that defines a resolution of 80,000 pixels to process a first subsequent captured image. Processor 540 may analyze at least one second image to determine a second image context (Step 970). For example, processor 540 may analyze a second image to determine the meaning of text written on a surface that appears in the second image. Processor 540 may select a second image capture resolution rule based on the determined second image context (Step 980). The second image capture resolution rule may define a second resolution, for example, 2 megapixels. Processor 540 may further apply the second image capture resolution rule to at least one second subsequent captured image (Step 990). For example, processor 540 may apply a resolution of 2 megapixels to the third, fourth, and fifth subsequent captured images. The second resolution may be greater than, lower than, or equal to the first resolution. For example, the second resolution may be 2 megapixels, and the first resolution may be 2 megapixels, greater than 2 megapixels, or lower than 2 megapixels.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks, floppy disks, or CD ROM, or other forms of RAM or ROM, USB media, DVD, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, C++, Objective-C, HTML, HTML/AJAX combinations, XML, or HTML with included Java applets. One or more of such software sections or modules can be integrated into a computer system or existing e-mail or browser software.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed routines may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. An apparatus comprising:
   an image sensor configured to capture real time images at a plurality of resolutions from an environment of a user;
   at least one processor device configured to:
   capture, at an initial resolution, a plurality of images from the image sensor;
   access rules associating image context with image capture resolution to enable images of a first context to be captured at a lower capture resolution than images of a second context;
   analyze at least one first image captured by the image sensor to determine a first image context;
   select a first image capture resolution rule based on the determined first image context, wherein the first image capture resolution rule defines a first resolution for capturing images in the environment of the user;
   apply the first image capture resolution rule to at least one subsequent captured image;
   analyze at least one second image captured by the image sensor to determine a second image context, wherein the second image context relates to text in the environment of the user;
   select a second image capture resolution rule based on the determined second image context, wherein the second image capture resolution rule defines a second resolution for capturing images in the environment of the user that include the text; and apply the second image capture resolution rule to at least one second subsequent captured image, wherein the second resolution is greater than the first resolution.

2. The apparatus of claim 1, wherein the image sensor is further configured to be connected to glasses worn by the user, and is thereby configured to be movable with a head of the user.

3. The apparatus of claim 1, further comprising a mobile power source, wherein the mobile power source is rechargeable and contained within a housing that holds the at least one processor device.

4. The apparatus of claim 1, wherein the at least one processor device is further configured to determine an existence of a trigger in at least one of the plurality of images, wherein the trigger is associated with an object in the environment of the user.

5. The apparatus of claim 4, wherein the at least one processor device is further configured to determine the context using at least one of: an identity of the object, a background of the object, a location of the trigger in the images, and information indicative of a location of the user.

6. The apparatus of claim 1, wherein the first image capture resolution is greater than the initial resolution.

7. The apparatus of claim 1, wherein the first image capture resolution is substantially equal to the initial resolution.

8. The apparatus of claim 1, wherein the initial resolution has resolution lower than 5 megapixels.

9. The apparatus of claim 1, wherein the initial resolution has resolution lower than 80,000 pixels.

10. The apparatus of claim 1, wherein the first image capture resolution is higher than 300,000 pixels.

11. The apparatus of claim 1, wherein the first image capture resolution is higher than 10 megapixels.

12. The apparatus of claim 1, wherein the first image capture resolution rule further defines a plurality of image portions, each image portion being associated with a differing resolution to be captured in the at least one subsequent captured image.

13. The apparatus of claim 1, wherein the first image capture resolution rule defines a plurality of image portions, and at least one image portion is not to be captured in the at least one subsequent captured image.

14. The apparatus of claim 1, wherein the first image capture resolution rule includes zoom information.

15. The apparatus of claim 1, wherein the at least one processor device is further configured to execute an action from multiple context-based actions, wherein the multiple context-based actions include at least one action associated with the first image capture resolution and at least one additional action associated with the second image capture resolution.

16. The apparatus of claim 1, wherein the at least one processor device is further configured to identify objects in images captured in the second image capture resolution.

17. The apparatus of claim 1, wherein the at least one processor device is further configured to execute optical character recognition on images captured in the second image capture resolution.

18. A method comprising:

capturing, by an image sensor, a plurality of images at an initial resolution from an environment of a user;

accessing rules associating image context with image capture resolution to enable images of a first context to be captured at a lower capture resolution than images of a second context;

analyzing at least one first image captured by the image sensor to determine a first image context;

selecting a first image capture resolution rule based on the determined first image context, wherein the first image capture resolution rule defines a first resolution for capturing images in the environment of the user;

applying the first image capture resolution rule to at least one subsequent captured image;

analyzing at least one second image captured by the image sensor to determine a second image context, wherein the second image context relates to text in the environment of the user;

selecting a second image capture resolution rule based on the determined second image context, wherein the second image capture resolution rule defines a second resolution for capturing images in the environment of the user that include the text; and applying the second image capture resolution rule to at least one second subsequent captured image, wherein the second resolution is greater than the first resolution.

19. The method of claim 18, wherein the first resolution is substantially equal to the initial resolution.

20. The method of claim 18, wherein the first resolution is greater than the initial resolution.

21. A software product stored on a non-transitory computer readable medium and comprising data and computer implementable instructions for carrying out the method of claim 18.

22. The apparatus of claim 1, further comprising a mobile power source.

23. The apparatus of claim 1, wherein the at least one processor device is further configured to determine an existence of a trigger in at least one of the plurality of images.

24. The method of claim 18, further comprising identifying an existence of a trigger in at least one of the plurality of images.

* * * * *